United States Patent [19]

Crivello

[11] Patent Number: 6,075,155

[45] Date of Patent: Jun. 13, 2000

[54] RADIATION-CURABLE CYCLOALIPHATIC EPOXY COMPOUNDS, USES THEREOF, AND COMPOSITIONS CONTAINING THEM

[75] Inventor: James V. Crivello, Clifton Park, N.Y.

[73] Assignee: Rensselaer Polytechnic Institute, Troy, N.Y.

[21] Appl. No.: 09/102,448

[22] Filed: Jun. 22, 1998

[51] Int. Cl.$^7$ .................. C07D 303/06; C07D 303/00; C07D 493/00; C07D 315/00; C07D 307/02

[52] U.S. Cl. .................. 549/544; 549/333; 549/336; 549/416; 549/475; 549/430; 549/545; 549/546; 549/547

[58] Field of Search .................. 549/544, 545, 549/546, 547, 416, 475, 430, 333, 336; 522/100, 170, 168, 169, 122; 528/413, 414, 411.1; 527/508, 516, 517

[56] References Cited

U.S. PATENT DOCUMENTS

| | | | |
|---|---|---|---|
| 2,543,419 | 2/1951 | Neiderhauser | 549/544 |
| 2,999,867 | 9/1961 | Starcher et al. | 549/526 |
| 3,117,852 | 1/1964 | Dissen | 549/524 |
| 3,155,689 | 11/1964 | Burton et al. | 526/268 |
| 3,230,202 | 1/1966 | Tinsley et al. | 526/78.5 |
| 3,274,126 | 9/1966 | Orinda | 528/124 |
| 3,428,612 | 2/1969 | Tinsley et al. | 528/361 |
| 3,436,408 | 4/1969 | Batzer et al. | 549/544 |
| 3,565,922 | 2/1971 | Rudy et al. | 549/546 |
| 3,968,070 | 7/1976 | Sundt | 549/332 |
| 4,036,629 | 7/1977 | Strong | 504/291 |
| 4,078,077 | 3/1978 | Brooks | 514/468 |
| 4,107,185 | 8/1978 | Strong | 549/546 |
| 4,140,847 | 2/1979 | Orvik et al. | 528/403 |
| 4,162,258 | 7/1979 | Higo et al. | 524/332 |
| 4,260,526 | 4/1981 | Kaiser et al. | 512/9 |
| 4,709,061 | 11/1987 | Brunke et al. | 549/544 |
| 4,882,445 | 11/1989 | Higa et al. | 549/546 |
| 5,155,243 | 10/1992 | Fujiwa et al. | 549/546 |

OTHER PUBLICATIONS

Crivello, J. et al., "Synthesis and Cationic Photopolymerization of 1-Butenyl Glycidyl Ether", Journal of Polymer Science: Part A: Polymer Chemistry, vol. 36, pp. 1179–1187 (1998).

Crivello, J. et al., "Synthesis and Photopolymerization of 1-Propenyl Glycidyl Ether", Journal of Polymer Science: Part A: Polymer Chemistry, vol. 32, pp. 1639–1648 (1994).

Crivello, J. et al., "The Photoinitiated Cationic Polymerization of Epoxy Resins", ACS Sypm. Ser. 114, 1, pp. 1–16 (1979).

Crivello, J. et al., "The Electron Beam–Induced Cationic Polymerization of Epoxy Resins", Journal of Applied Polymer Science, vol. 44, 9–16 (1992).

Crivello, J. et al., Preparation of 1-Propenyl Ether Functional Siloxanes by Chemoselective Hydrosilation and Their Cationic Photopolymerization:, Macromolecules, vol. 28, pp. 8057–8064 (1995).

Crivello, J. et al., "Mechanistic Study of the Reactivity of 3′,4′-Epoxycyclohexancarboxylate in Photoinitiated Cationic Polymerization", Journal of Polymer Science: Part A: Polymer Chemistry, vol. 33, 2473–2486(1995).

Crivello, J. et al., "Regioselective Hydrosilations. III. The Synthesis and Polymerization of Ambifunctional Silicon–Containing Epoxy Monomers", Journal of Polymer Science: Part A: Polymer Chemistry, vol. 31, 3109–3119 (1993).

Crivello, J. et al., "Novel Epoxynorbornane Monomers. 1. Synthesis and Characterization", Macromolecules, vol. 29, pp. 43–438 (1996).

Crivello, J. et al., "Synthesis and Cationic Polymerization of Open–Chain and Cyclic Enol Ethers", Macromolecular Science, Part A, vol. 33(6), pp. 717–735(1996).

Akhtar, S. et al., "Synthesis of Aryl–Substituted Sulfonium Salts by the P205–Methanesulfonic Acid Promoted Condensation of Sulfoxides with Aromatic Compounds", J. Org. Chem. vol. 55, pp. 4222–4225, (1990).

Crivello, J. et al., "Novel Epoxynorbornane Monomers. 2. Cationic Photopolymerization", Macromomolecules (1996) vol. 29, pp. 439–445 (1996).

Crivello, J. et al., "Aromatic Bisvinyl Ethers: A New Class of Highly Reactive Thermosetting Monomers", Journal of Polymer Science: Polymer Chemistry Edition, vol. 21, 1785–1799 (1983).

Crivello, J. "Photo and Thermal Catalysts for Cationic Polymerization", Chapter 5 of J.V. Crivello: Ring–Opening Polymerization, D.J. Brunelle, editor, Hansen Pub; p 157–196.

Primary Examiner—James J. Seidleck
Assistant Examiner—Sanza L. McClendon
Attorney, Agent, or Firm—Scully, Scott, Murphy & Presser

[57] ABSTRACT

Disclosed are compounds of the formulas

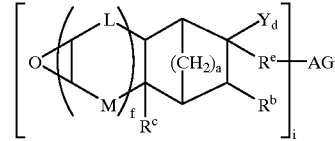
(1)

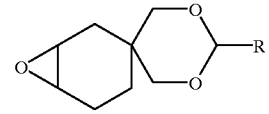

(2)

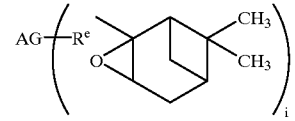

(3)

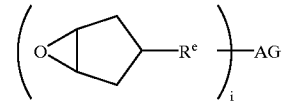

(4)

which are useful as monomers in photopolymerizable compositions. Also disclosed are methods of polymerizing these monomers, and polymers produced thereby.

68 Claims, 7 Drawing Sheets

RADIATION-CURABLE CYCLOALIPHATIC EPOXY COMPOUNDS, USES THEREOF, AND COMPOSITIONS CONTAINING THEM

FIELD OF THE INVENTION

The present invention relates to novel radiation-curable cycloaliphatic epoxy compounds, to radiation-curable compositions containing such compounds, and to processes for forming radiation-cured products from such compounds and compositions.

BACKGROUND OF THE INVENTION

Radiation curing has become an important and useful technique for applying and curing coatings, inks, and adhesives. As described herein, radiation curing involves presenting a radiation-curable monomer, typically in combination with a photo-initiator, and exposing the composition to radiation in the form of ultraviolet or electron-beam radiation to cause the radiation-curable compound to polymerize.

Radiation curing presents many advantages, such as high rates of throughput, low energy requirements, and low equipment costs. In addition, it is advantageous that users are able to avoid using a solvent when the composition to be radiation-cured is prepared. Solvents typically would lead to environmental and/or safety hazards, and would require additional equipment and handling steps to remove the solvent.

There remains a need for radiation-curable compounds, photopolymerizable or otherwise, which provide improved polymerizability and which can be formulated into a variety of coatings, films and the like readily and rapidly.

BRIEF SUMMARY OF THE INVENTION

The present invention is directed to compounds which contain 1 to 3 cycloaliphatic epoxy groups and an oxidizable group containing an ether linkage or an ethylenic or acetylenic bond, and which undergo photopolymerization when exposed to ultraviolet, electron beam or X-ray irradiation in the presence of a photoinitiator.

Included among these are compounds of formulas (1), (2), (3) and (4):

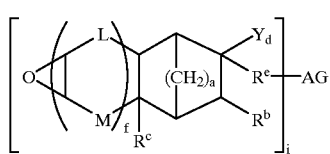

(1)

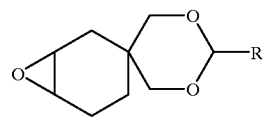

(2)

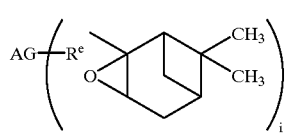

(3)

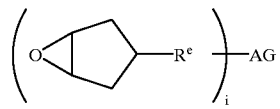

(4)

wherein i is 1, 2, or 3;
$R^b$ is hydrogen or straight or branched alkyl containing 1 to 20 carbon atoms;
$R^c$ is hydrogen or straight or branched alkyl containing 1 to 20 carbon atoms;
$R^e$ is a single bond or straight or branched divalent alkyl containing 1 to 20 carbon atoms;
a is 0 or 1, and f is 0 or 1;
Y is hydrogen or straight or branched alkyl containing up to 12 carbon atoms;
one of L and M is —$CH_2$— and the other is a single bond;
when i is 1, AG is —OM or a monovalent heterocyclic group containing 3, 4 or 5 carbon atoms and 1 or 2 oxygen atoms, wherein M is straight or branched alkyl containing 2 to 20 carbon atoms which contains a C=C bond, a C≡C bond, or an ether oxygen, or M is phenyl, benzyl, or a monovalent heterocyclic group containing 3, 4 or 5 carbon atoms and 1 or 2 oxygen atoms, and AG is optionally substituted with an R group;
when i is 2, AG is —O—D—O— wherein D is divalent straight or branched alkyl containing up to 20 carbon atoms which optionally contains a C=C bond or a C≡C bond, and which is optionally substituted with an R group, wherein D can optionally be interrupted with an ether oxygen, $C_6H_4$ phenylene, or cycloalkyl containing 2 to 20 carbon atoms and 0–2 oxygen atoms;
when i is 3, AG is —O—T(—O—)—O—, wherein T is trivalent straight or branched alkyl containing up to 25 carbon atoms which optionally contains a C=C bond or a C≡C bond, wherein T can optionally be interrupted with an ether oxygen; or T is a cycloalkyl group of 3 to 25 carbon atoms or a phenyl group and is substituted with 3 groups each independently having the formula $C_tH_{2t}$, wherein t is 1 to 20;
R is phenyl optionally substituted with a G group, or cycloalkyl or cycloalkyl-alkyl containing 5 to 25 carbon atoms wherein up to 2 ring carbon atoms are replaced with oxygen atoms, and R is optionally substituted with a G group; and
G is alkyl containing 1 to 20 carbon atoms, —CHO, alkoxy containing 1 to 20 carbon atoms, cycloalkoxy or cycloalkyl containing 5 to 25 carbon atoms, —COOH, —$NO_2$, phenyl, halo, or vinyl.

Another aspect of the present invention is compositions comprising one or more of said compounds of formulas (1)–(4) and also comprising one or more photoinitiators in an amount effective to mediate polymerization of said compound when the composition is irradiated with, for instance, ultraviolet radiation or electron beam radiation or X-ray radiation.

Yet another aspect of the present invention is a process of forming a polymeric structure, such as a coating, film, or solid body, comprising forming the aforementioned composition of one or more compounds of formula (1)–(4) and a photoinitiator, and then irradiating the composition with ultraviolet, or X-ray or electron beam radiation effective to polymerize said one or more compounds of formula (1)–(4).

Methods of making the aforementioned compounds are also within the scope of the present invention.

DETAILED DESCRIPTION OF THE INVENTION

Figure 1:
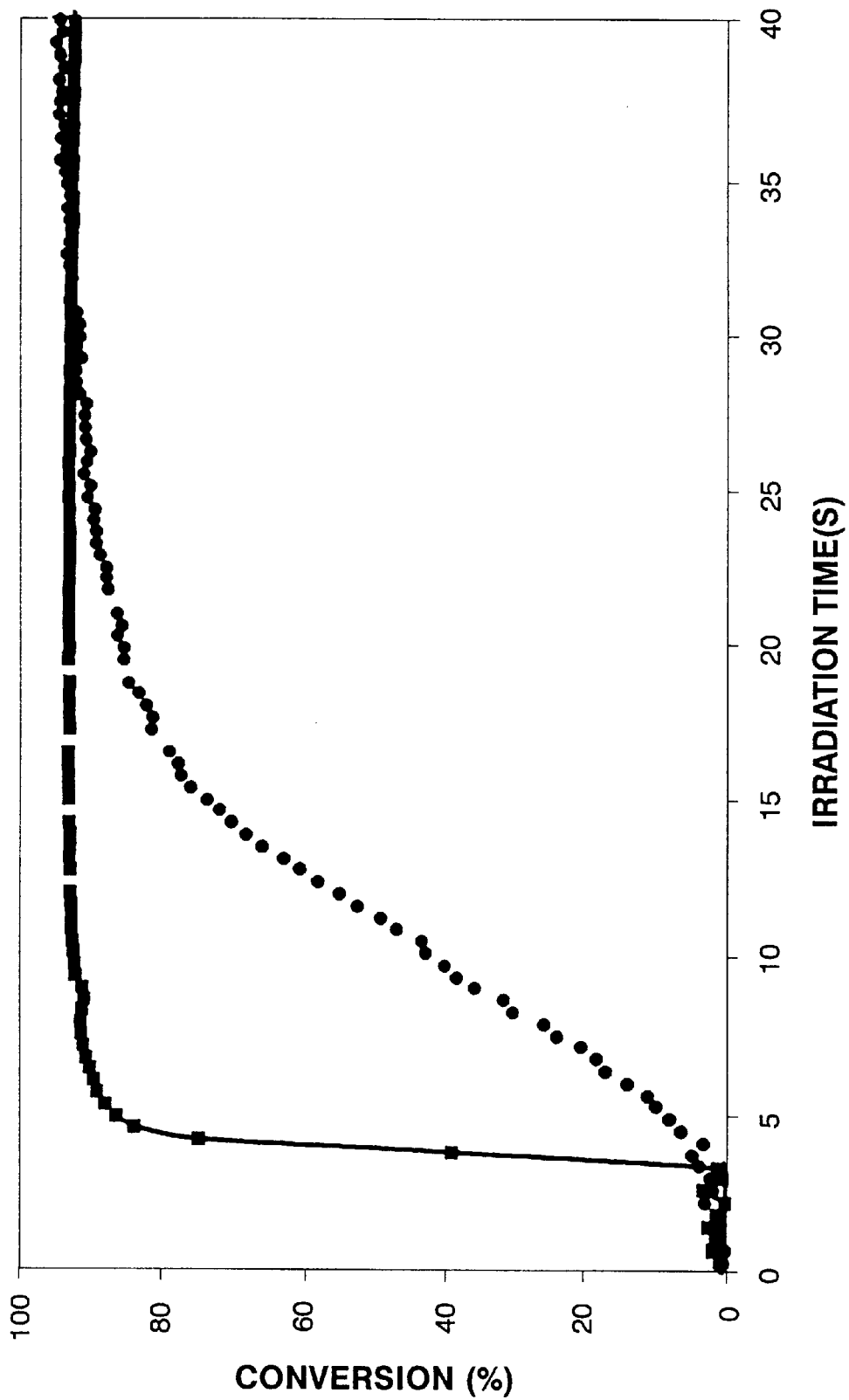
FIGS. 1–7 are graphs of the extent of polymerization over time for several monomers prepared in the Examples.

Referring first to formula (1), the molecule can be unbridged cyclohexyl-epoxy, as when a and f both are zero. The molecule can be bicyclic, when one of a or f is one and the other is zero; and it can be polycyclic, when both a and f equal one. It can be seen that if f is one, the cyclic moiety to which the epoxy oxygen is attached is always cyclopentyl, regardless of whether L or M represents —CH$_2$—, since either one of those linkages is always —CH$_2$— and the one that is not —CH$_2$— is a single bond.

The substituents $R^b$ and $R^c$ can each be hydrogen, which represents one preferred embodiment of the invention. One or both of $R^b$ and $R^c$ can be straight or branched alkyl containing up to 20 carbon atoms, and preferably up to 6 carbon atoms, especially methyl, ethyl, isopropyl or n-propyl.

The substituent Y is hydrogen or straight or branched alkyl containing up to 12 carbon atoms and preferably up to 6 carbon atoms, especially methyl, ethyl, isopropyl or n-propyl.

Referring to formulas (1), (3) and (4), the linkage $R^e$ connecting the cyclic moiety with the group AG can be a single bond, which is one preferred embodiment of the invention. $R^e$ can also be straight or branched alkyl, containing up to 20 carbon atoms, such as —(CH$_2$)$_{1-6}$, isopropyl, or more generally —CHR*R**— wherein R* and R** are alkyl groups or one is hydrogen.

The substituent R shown in formula (2), but also optionally present in group AG, is preferably phenyl or cycloalkyl containing 5 to 25 carbon atoms but more preferably 5 or 6 carbon atoms, 1 or 2 of which can be replaced by oxygen atoms.

Turning to the group AG, a considerable variety of structures can be used. One type of structure is —OM wherein M is straight or branched monovalent or divalent alkyl containing 2 to 20 carbon atoms, more preferably 2 to 6 carbon atoms, and optionally containing ethylenic or acetylenic unsaturation. Examples of such M groups include:

—CH$_2$CH=CH$_2$
—CH$_2$CH=CHCH$_3$
—CH$_2$C(CH$_3$)=CH$_2$
—CH$_2$CH=CHC$_6$H$_5$
—CH=CHCH$_3$
—CH(CH$_3$)CH=CH$_2$
—CH$_2$CH$_2$CH=CH$_2$
—CH$_2$C≡CH
—CH=CH$_2$

Other useful monovalent AG groups contain an ether oxygen, or are heterocyclic. Examples of —OM groups with ether oxygen include those wherein M is:

—CH$_2$OCH$_3$
—CH$_2$OCH$_2$CH$_3$
—CH$_2$OR, e.g. —CH$_2$OC$_6$H$_5$
—CH(CH$_3$)OCH$_3$
—CH(CH$_3$)OR, e.g. —CH(CH$_3$)OC$_6$H$_5$
—CH(C$_2$H$_5$)OCH$_3$
—CH(C$_2$H$_5$)OR e.g. —CH(C$_2$H$_5$)OC$_6$H$_5$
—CH$_2$CH$_2$OCH$_2$C$_6$H$_5$

Examples of heterocyclic M or AG groups include tetrahydrofuryl, dioxolanyl, furfuryl, tetrahydrofurfuryl and oxanyl.

Examples of divalent D groups include:

—CH$_2$CH=CHCH$_2$—
—CH=CHCH$_2$CH$_2$—
—CH$_2$C≡CCH$_2$—Other useful divalent D groups include —CH$_2$C$_6$H$_4$CH$_2$—, —CH(C$_6$H$_5$)—, and —(CH$_2$)$_{1-4}$—.

As noted, AG can also be trivalent. Examples of T groups include all trivalent analogs of the foregoing M and D groups. One preferred example is 1, 3, 5-trimethylphenyl.

Examples of specific compounds according to the present invention include the following:

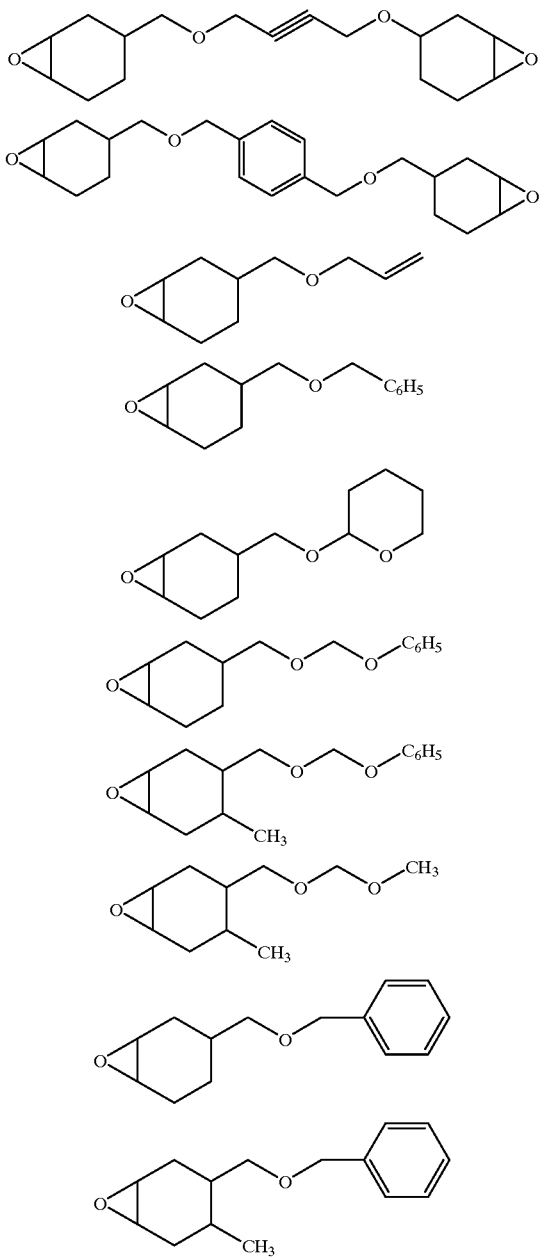

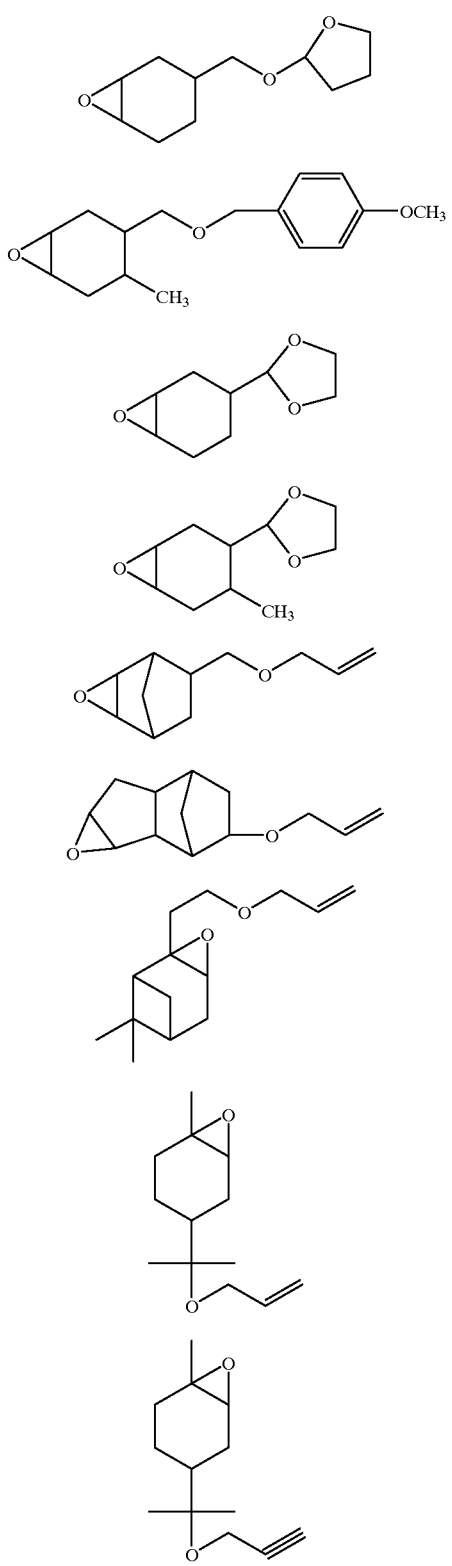
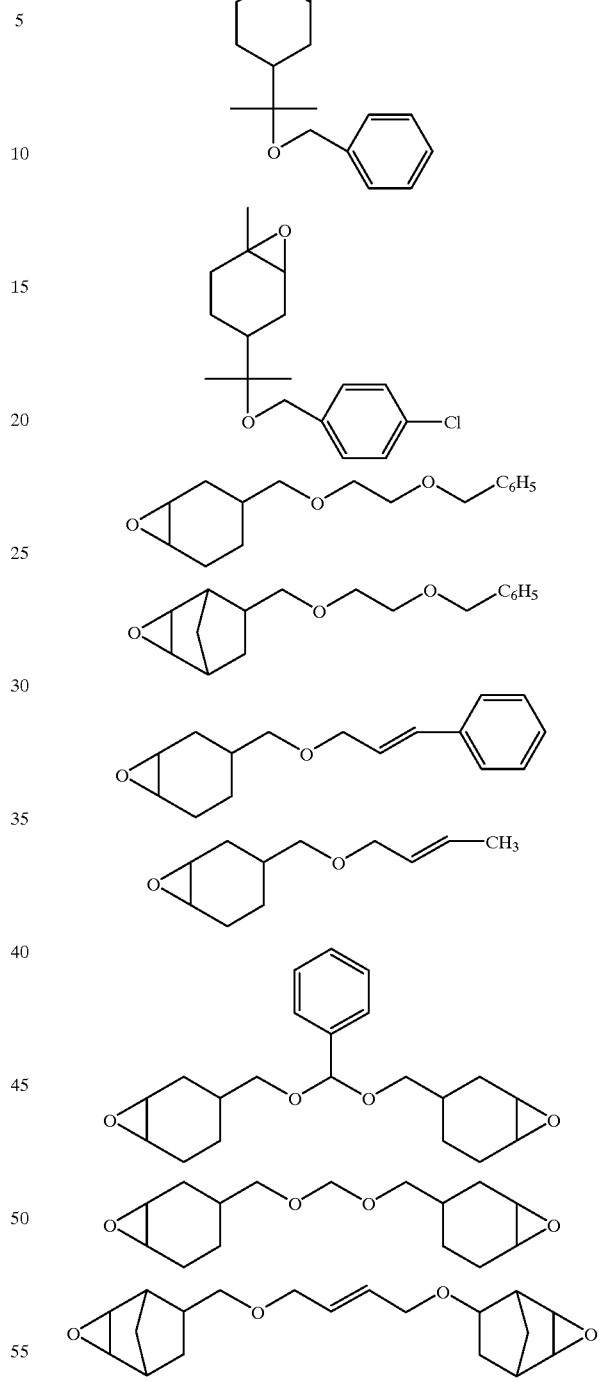
The epoxy compounds of the present invention are synthesized by methods that are straightforward. In general, the methods for synthesis of compounds wherein AG has the formula —OM, —ODO— or —O—T(O—)—O—, involve (1) formation of an ether (Int)$_i$-AG wherein (Int) is a cyclic alkenyl precursor of the eventual cyclic epoxy moiety, and i and AG are as defined herein; followed by (2) epoxidation of the C=C bond on the cyclic alkenyl precursor.

The ether formation can proceed via reaction of a hydroxyl-terminated reactant (Int)-OH with a compound (AG')-X wherein (AG') is analogous to AG but lacks the terminal oxygen atom, and X is a leaving group such as bromide which is in the position to be occupied by that oxygen. Such reactions, as is known, proceed under alkaline conditions.

The ether formation can instead proceed via reaction of a hydroxy reactant (AG-H) with an ethylenically unsaturated analog of a compound of formula (Int), whereby the hydroxyl group on (AG-H) adds across the ethylenic unsaturation to form (Int)$_i$-AG. Such reactions, as is known, proceed under acidic conditions.

Epoxidations of the cyclic alkenyl intermediate can proceed by established techniques such as reaction with m-chloroperbenzoic acid, peracetic acid, hydrogen peroxide, or other strongly oxidizing reagent.

Examples of typical synthetic pathways include the following:

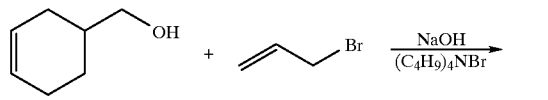
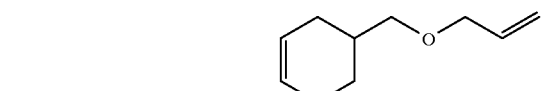
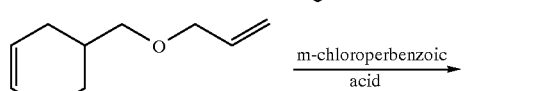
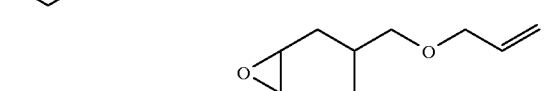

$MTTP=[(C_8H_{17})_3N(CH_3)]_3{}^+[PO_4(W(O)(O_2)_2)_4]^3$

Compounds of the formula (1) wherein AG is a monovalent heterocyclic group containing one or two ring oxygen atoms can be synthesized by (1) reaction of a cyclic alkenyl precursor having a pendant aldehyde group, with respectively a monol or diol containing one carbon atom fewer than the number of carbon atoms in the intended ring, under acidic conditions with removal of byproduct water, followed by (2) epoxidation of the alkenyl site. An example of such a reaction scheme is:

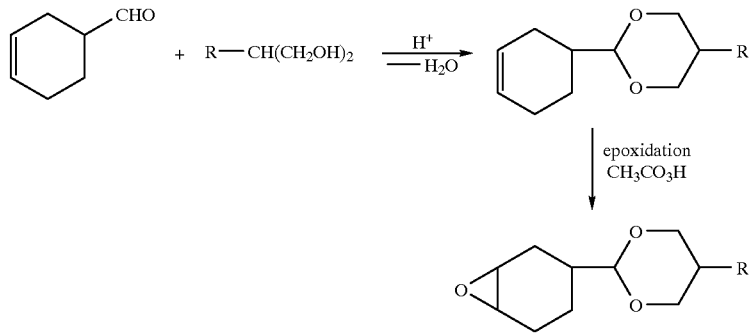

Compounds of formula (2) can be prepared by (1) reaction of bis(hydroxymethyl) cyclohexene with an aldehyde R—CHO, under acidic conditions with removal of byproduct water, followed by (2) epoxidation of the alkenyl site. The reaction scheme can be illustrated as:

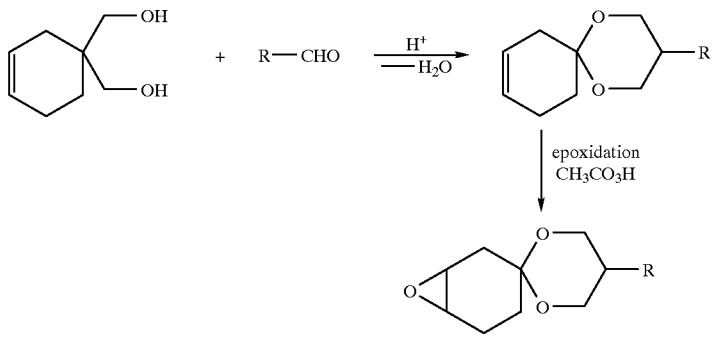

The epoxy compounds of the present invention are readily polymerized by exposure to ultraviolet, or X-ray or electron beam radiation in the presence of a cationic photoinitiator. Among those photoinitiators which may be used to achieve polymerization are diazonium salts, diaryliodonium salts, triarylsulfonium salts, diaryliodosonium salts, triarylsulfoxonium salts, dialkylphenacylsulfonium salts, ferrocenium salts and dialkyl-4-hydroxyphenylsulfonium salts. Typically, these salts contain complex metal halide or other non-nucleophilic ions such as $BF_4^-$, $PF_6^-$, $SbF_6^-$, $AsF_6^-$, $ClO_4^-$, $CF_3SO_3^-$, $(C_6F_5)_4B^-$ and the like. Examples of suitable photoinitiator salts are described hereinbelow and include those described in Crivello and Dietliker, in *Chemistry & Technology of UV & EB Formulation For Coatinas, Inks & Paints*, Vol. 3, 1991, page 329, the disclosure of which is hereby incorporated herein by reference.

The preferred photoinitiators are diaryliodonium salts and phenacylsulfonium salts. Also preferred are sulfonium salts of the formula Ar—C(O)CH$_2$S$^+$R'R"X$^-$ wherein Ar is monocyclic or bicyclic aryl or substituted aryl, such as phenyl, naphthyl, biphenyl, anthracenyl, phenanthryl, or heterocyclic such as furanyl or thiophenyl; R' and R" are the same or different and are alkyl, cycloalkyl or aromatic, and X$^-$ is a non-nucleophilic anion as described above.

The amount of photoinitiator should be in the range of about 0.1 to 10% by weight based on the weight of the epoxy compound or compounds. As noted herein, the compositions containing such epoxy compounds and one or more photoinitiators for polymerization of such compounds comprise one aspect of the present invention.

Rapid and complete polymerization of the epoxy compounds can be achieved by irradiating the composition with an electron beam or x-ray dose on the order of 0.1 to 10 Mrad or ultraviolet radiation flux on the order of 10–30 mW/cm$^2$. Higher energy levels are also useful, especially when higher throughput speeds are desired or thicker masses of polymer are presented.

Photopolymerizable compositions containing the epoxy compounds of the present invention can also contain any of the other additives customary for such uses, in the amounts thereof adequate to enable the additive to perform its desired function. Such additives include photosensitizers, fillers, flow control agents and the like. Examples of suitable materials for providing these functions abound in this field and are well known to those experienced in this field, and include the materials which are employed for those functions with other radiation-curable monomers such as acrylates and vinyl ethers. In addition, other comonomers may be present such as epoxies, vinyl ethers and 1-butenyl ethers.

Films and coatings formed by irradiation of compositions containing any of the epoxy compounds of exhibit satisfactory and even superior mechanical strength, adhesion to substrate, high temperature stability, and high reactivity. It is not necessary to formulate the photo-polymerizable or electron beam-polymerizable composition in a solvent, thus permitting the operator to avoid the hazards and inconvenience of using solvents.

EXAMPLES $^1$H NMR spectra were obtained using Varian XL-200 and XL-500 spectrometers at room temperature in CDCl$_3$. All chemical shifts are reported relative to tetramethylsilane as an internal standard. Gas chromatographic (GC) analyses were performed on a Hewlett Packard HP-5840A gas chromatograph equipped with a 15 m×0.53 mm×1.5 mm film thickness crosslinked methyl silicone gum column and a flame ionization detector. Differential scanning calorimetry (DSC) and thermogravimetric analysis (TGA) measurements were carried out under a nitrogen atmosphere at heating rates of 5° C./min and 20° C./min respectively using a Perkin-Elmer DSC-7 TGA-7 Thermal Analysis System. Elemental analyses were performed by Atlantic Microanalysis, Inc. (Norcross, Ga.).

Example 1
Synthesis of (2-Oxapent-4-enyl)cyclohex-3-ene (CA)
Method A

Into a 500 mL round bottom flask equipped with an overhead stirrer, thermometer and a nitrogen inlet were placed 56.085 g (0.5 mol) of distilled 1,2,3,6-tetrahydrobenzylalcohol, 90.75 g (0.75 mol) of allyl bromide, 100 mL of toluene and 30 g (0.75 mol) of sodium hydroxide. The reaction mixture was stirred at room temperature for 15 minutes. Then, 3 g (0.01 mol) of tetra-n-butylammonium bromide was added and the reaction mixture slowly heated to reflux (65° C.) and maintained at that temperature for eight hours. The reaction mixture was cooled and filtered to remove the sodium bromide which precipitated during the reaction. The filtrate was poured into 500 mL of distilled water, the organic layers were separated and the aqueous layer extracted with fresh toluene. The combined organic layers were washed with three 200 mL portions of distilled water and the organic phase was dried over anhydrous sodium sulfate. Then, the excess allyl bromide and toluene were removed using a rotary evaporator and the reaction mixture subjected to vacuum distillation.

The clear liquid distillate amounted to 62.32 g (82% recovered yield). Fractional vacuum distillation gave pure CA with a boiling point of 22° C. at 0.05 mm Hg.

$^1$H NMR (CDCl$_3$): δ (ppm) 1.1–1.4 (H$_1$, 1H); 1.5–2.3 (H$_2$+H$_5$+H$_6$, 6H); 3.15–3.5 (H$_7$, 2H); 3.8–4.1 (H$_8$, 2H); 5.1–5.4 (H$_{10}$, 2H); 5.5–5.8 (H$_3$+H$_4$, 2H); 5.8–6.1 (H$_9$, 1H).

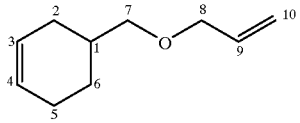

Elemental Analysis. Calculated for C$_{10}$H$_{16}$O: C, 78.90%; H, 10.59%. Found: C, 78.82%; H, 10.52%.

Method B

Into a 250 mL round bottom flask equipped with a magnetic stirrer were placed 14.0 g (0.127 mol) of distilled 1,2,3,6-tetrahydrobenzaldehyde, 60 mL (0.869 mol) of allyl alcohol and 16.24 g (0.14 mol) of triethylsilane. The reaction mixture was stirred at 0° C. for 1 h. Then, 25 mL of concentrated sulfuric acid were added dropwise over a period of 1 h using an addition funnel. The reaction mixture was slowly warmed to room temperature and maintained at that temperature for 1 h. To the above cooled reaction mixture, 100 mL of pentane was added. This mixture was washed thrice with 100 mL of a saturated solution of sodium chloride. The organic layer was separated and dried over sodium sulfate. The excess allyl alcohol and pentane were removed using a rotary evaporator and the reaction mixture subjected to fractional vacuum distillation. The resulting clear liquid amounted to 12.8 g (73% recovered yield). Fractional distillation gave pure CA with a boiling point of 22° C. at 0.05 mm Hg.

The $^1$H NMR of the CA obtained by Method B was similar to that obtained by Method A.

Elemental Analysis. Calculated for C$_{10}$H$_{16}$O: C, 78.9%; H, 10.59%. Found: C, 78.79%; H, 10.57%.

Synthesis of 1(2-Oxapent-4-enyl)-6-methylcyclohex-3-ene (MCA)

A procedure analogous to that employed for CA (Method A) was used to synthesize MCA. A yield of 89% was obtained. The compound had a boiling point of 28° C. at 0.1 mm Hg.

$^1$H NMR (CDCl$_3$): δ (ppm) 0.7–1.1 (H$_1$+H$_7$,4H); 1.5–2.4 (H$_2$+H$_5$+H$_6$, 6H); 3.2–3.6 (H$_8$, 2H); 3.8–4.1 (H$_9$, 2H); 5.1–5.4 (H$_{11}$, 2H); 5.5–5.75 (H$_3$+H$_4$, 2H); 5.8–6.1 (H$_{10}$,1H).

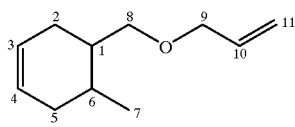

Elemental Analysis. Calculated for C$_{11}$H$_{17}$O: C, 79.95%; H, 10.37%. Found: C, 79.90%; H, 10.32%.

Synthesis of (2-Oxapent-4-enyl)bicylo [2.2.1] hept-5-ene (NA)

NA was prepared using the same procedure employed for CA (Method A). A yield of 90% was obtained. The compound had a boiling point of 35° C. at 0.05 mm Hg. $^1$H NMR (CDCl$_3$): δ (ppm) 0.3–0.5 (H$_{6n}$, 1H); 0.9–1.2 (H$_{7anti}$, 1H); 1.25–1.4 (H$_{7syn}$, 1H); 1.5–1.9 (H$_{6x}$, 1H); 2.1–2.4 (H$_5$, 1H); 2.6–3.5 (H$_1$+H$_4$+H$_8$, 4H); 3.8–4.1 (H$_9$, 2H); 5.0–5.4 (H$_{11}$, 2H); 5.8–6.0 (H$_{10}$, 1H); 6.0–6.3 (H$_2$+H$_3$, 2H).

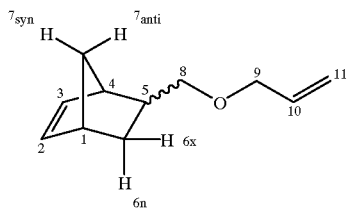

Elemental Analysis. Calculated for C$_{11}$H$_{16}$O: C, 80.44%; H, 9.82%. Found: C, 80.41%; H, 9.81%.

Example 2

Synthesis of (2-Oxapent-3-enyl)cyclohex-3-ene (CP)

To 19 g (0.125 mol) of CA in a 100 mL round bottom flask equipped with a magnetic stirrer, reflux condenser and a nitrogen inlet were added 0.008 g (0.0075 mmol) of tris (triphenylphosphine)ruthenium(II) dichloride. The reaction mixture was heated at 160° C. for 2 h. The $^1$H NMR spectrum showed that the bands assigned to the allyl groups (δ ppm 5.1–5.4, CH$_2$=; 5.8–6.1, CH=; 3.8–4.1, CH$_2$) had been completely replaced by new bands (δ ppm 1.58, CH$_3$; 4.25–4.45, cis-CH$_3$—C$\underline{H}$=; 4.65–4.85, trans-CH$_3$—C$\underline{H}$=; 5.9–6, cis-CH—O; 6.15–6.3, trans-O—CH) assigned to the 1-propenyl ether groups. Pure CP (mixture of d,l-cis and d,l-trans isomers) was isolated by fractional vacuum distillation (b.p. 156° C. at 20 mm Hg) in 92% yield.

Elemental Analysis. Calculated for C$_{10}$H$_{16}$O: C, 78.9%; H, 10.59%. Found: C, 78.79%; H, 10.53%.

Synthesis of (2-Oxapent-3-enyl)-6-methylcyclohex-3-ene (MCP)

The same procedure used for CP was used to synthesize MCP. A yield of 95% was obtained. The compound had a boiling point of 130° C. at 10 mm Hg.

$^1$H NMR (CDCl$_3$): δ (ppm) 0.8–1 (H$_1$+H$_7$,4H); 1.5–1.6 (H$_{11}$, 3H); 1.6–2.3 (H$_2$+H$_5$+H$_6$, 5H); 3.4–3.8 (H$_8$, 2H); 4.3–4.5 (H$_{10Z}$); 4.7–4.9 (H$_{10E}$) 5.6–5.8 (H$_3$+H$_4$, 2H); 5.9–6 (H$_{9Z}$); 6.2–6.3 (H$_{9E}$).

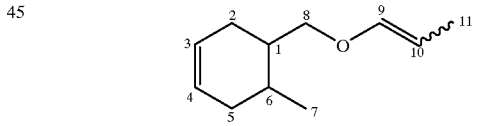

Elemental Analysis. Calculated for C$_{11}$H$_{17}$O: C, 79.95%; H, 10.37%. Found: C, 79.83%; H, 10.28%.

Synthesis of (2-Oxapent-3-enyl)bicylo [2.2.1] hept-5-ene (NP)

A procedure analogous to CP was used to synthesize NP. Complete disappearance of the bands assigned to the allyl groups (δ ppm 5.0–5.4, CH$_2$=; 5.8–6.0, CH=; 3.7–4.0, CH$_2$) occurred only after 8 h of reaction. A yield of 94% of pure NP (cis endo and exo isomers only) was obtained. NP had a boiling point of 172° C. at 25 mm Hg.

$^1$H NMR (CDCl$_3$): δ (ppm) 0.3–0.5 (H$_{6n}$, 1H); 0.9–1.2 (H$_{7anti}$, 1H); 1.25–1.4 (H$_{7syn}$, 1H); 1.4–1.6 (H$_{11}$, 3H); 1.65–1.95 (H$_{6x}$, 1H); 2.2–2.5 (H$_5$, 1H); 2.7–3.5 (H$_1$+H$_4$+H$_8$, 4H); 4.3–4.5 (H$_{10}$, 1H); 5.9–6.0 (H$_{9E}$, 1H); 6.0–6.3 (H$_2$+H$_3$, 2H).

Elemental Analysis. Calculated for $C_{11}H_{16}O$: C, 80.44%; H, 9.82%. Found: C, 80.42%; H, 9.77%.

Example 3

Synthesis of (2-Oxapent-4-enyl)-3,4-epoxycyclohexane (CEA)

Into a 1 L round bottom flask equipped with an overhead stirrer, an addition funnel and a thermometer were placed 32.3 g of 3-chloroperoxybenzoic acid (0.1205 mol) and 300 mL methylene chloride. The flask was cooled to 0–3° C. using an ice bath. CA (20 g, 0.1205 mol) in 150 mL methylene chloride was added dropwise so that the temperature did not rise above 10° C. The addition required approximately 90 minutes. The reaction was allowed to warm to room temperature and then stirred overnight. The reaction mixture was filtered using a Büchner funnel to remove 3-chlorobenzoic acid and the filtrate washed with 100 mL quantities of saturated sodium bicarbonate solution until the evolution of carbon dioxide ceased. The organic layer was dried over anhydrous sodium sulfate. Then, the excess methylene chloride was removed using a rotary evaporator and the reaction mixture subjected to vacuum distillation. The volatile clear liquid amounted to 13.96 g (69% recovered yield). Fractional distillation gave pure CEA as a mixture of isomers with a boiling point of 30° C. at 0.1 mm Hg.

$^1$H NMR (CDCl$_3$): δ (ppm) 0.8–1.35 ($H_1$, 1H); 1.35–2.3 ($H_2+H_5+H_6$, 6H); 3.0–3.5 ($H_7+H_3+H_4$, 4H); 3.8–4.1 ($H_8$, 2H); 5.0–5.4 ($H_{10}$, 2H); 5.7–6 ($H_9$, 1H).

Elemental Analysis. Calculated for $C_{10}H_{16}O$: C, 71.39%; H, 9.59%. Found: C, 71.36%; H, 9.55%.

Example 4

Synthesis of (2-Oxapent-4-enyl)-6-methyl-3,4-epoxycyclohexane (MCEA)

An epoxidation procedure identical to that employed for CEA was used to synthesize MCEA. A yield of 70% was obtained. The mixture of isomers had a boiling point of 30° C. at 0.1 mm Hg.

$^1$H NMR (CDCl$_3$): δ (ppm) 0.8–1.0 ($H_1+H_7$, 4H); 1.35–2.3 ($H_2+H_5+H_6$, 5H); 3.0–3.5 ($H_3+H_4+H_8$, 4H); 3.8–4.1 ($H_9$, 2H); 5.0–5.0 ($H_{11}$, 2H); 5.7–6.05 ($H_{10}$, 1H).

Elemental Analysis. Calculated for $C_{11}H_{17}O_2$: C, 72.89%; H, 9.45%. Found: C, 72.85%; H, 9.45%

Example 5

Synthesis of (2-Oxapent-3-enyl)-3,4-epoxycyclohexane (CEP)

CEA was isomerized using a procedure identical to that used for CP. The isomerization reaction was complete after 9 h at 160° C. A yield of 93% was obtained. CEA (mixture of 8 isomers) had a boiling point of 165° C. at 22 mm Hg.

$^1$H NMR (CDCl$_3$): δ (ppm) 0.9–1.35 ($H_1$, 1H); 1.35–2.3 ($H_2+H_5+H_6+H_{10}$, 9H); 3.1–3.3 ($H_3+H_4$, 2H); 3.3–3.8 ($H_7$, 2H); 4.25–4.5 ($H_{9Z}$); 4.65–4.95 ($H_{9E}$); 5.8–6.0 ($H_{8Z}$); 6.1–6.3 ($H_{8E}$,)

Elemental Analysis. Calculated for $C_{10}H_{16}O_2$: C, 71.39%; H, 9.59%. Found: C, 71.39%; H, 9.53%.

Example 6

Synthesis of (2-Oxapent-3-enyl)-6-methyl-3,4-epoxycyclohexane (MCEP)

An isomerization procedure analogous to CP was utilized for the synthesis of MCEP. The isomerization reaction was complete after 8 h at 160° C. A yield of 94% of MCEP was obtained. The isomeric mixture had a boiling point of 142° C. at 15 mm Hg.

$^1$H NMR (CDCl$_3$): δ (ppm) 0.7–1.05($H_1+H_7$, 4H); 1.1–2.3 ($H_2+H_5+H_6+H_{11}$, H.); 3.0–3.3 ($H_3+H_4$, 2H); 3.3–3.8 ($H_8$, 2H); 4.25–4.5 ($H_{10Z}$); 4.7–4.9 ($H_{10E}$); 5.8–6.0 ($H_{9Z}$); 6.1–6.3 ($H_{9E}$,).

Elemental Analysis. Calculated for $C_{11}H_{17}O_2$: C, 72.89%; H, 9.45%. Found: C, 72.82%; H, 9.39%

Example 7

Synthesis of (2-Oxapent-4-enyl)-3-oxatricylo [3.2.1.0$^{2,3}$] hept-5-ene (NEA)

Regioselective epoxidation of NA was conducted using a procedure described in Crivello and Narayan, Macromolecules, 29, 431 (1996) to synthesize NEA. In a 3L three-neck round bottom flask equipped with a mechanical stirrer, two pressure equalizing addition funnels and a thermometer were placed 20 g (0.1217 mol) of NA, 100 mL of acetone, 100 mL of dichloromethane, 500 mL of a phosphate buffer and 0.5 g of 18-crown-6. The flask was cooled to 0° C. using a salt/ice/water bath and 65 g of Oxone® (2KHSO$_5$, K$_2$SO$_4$, KHSO$_4$) was added as a 0.4 M ice-cold, clear aqueous solution using one addition funnel. The pH of the solution was monitored using a narrow range pH(7.2–8.8) paper and was maintained at 7.4–7.6 using 1N sodium hydroxide solution from the second addition funnel. After addition of Oxone® solution was completed, the reaction was stirred at 5° C. for an additional 5–6 h. The product was filtered to remove precipitated solids, and the organic and aqueous layers were separated. The aqueous layer was extracted with four 100 mL quantities of dichloromethane and the combined organic layers were washed with four 100 mL aliquots of distilled water. The organic layer was dried over anhydrous sodium sulfate, and the solvent was removed using a rotary evaporator. Distillation under reduced pressure gave NEA (60% yield) as a colorless liquid with a boiling point of 40° C./0.05 mm Hg.

$^1$H NMR (CDCl$_3$): δ (ppm) 0.5–0.85 (H$_{6n}$, 1H); 0.9–1.2 (H$_{7anti}$, 1H); 1.25–1.4 (H$_{7syn}$, 1H); 1.5–1.9 (H$_{6X}$, 1H); 2.1–2.4 (H$_5$, 1H); 2.4–2.6 (H$_1$+H$_4$, 2H); 3.0–3.3 (H$_2$+H$_3$, 2H); 3.3–3.5 (H$_8$, 2H); 3.8–4.1 (H$_9$, 2H); 5.0–5.4 (H$_{11}$, 2H); 5.8–6.1 (H$_{10}$, 1H); 6.0–6.3 (H$_2$+H$_3$, 2H)

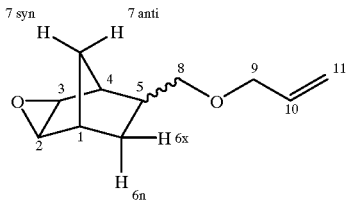

Elemental Analysis. Calculated for C$_{11}$H$_{16}$O$_2$: C, 73.30%; H, 8.95%. Found: C, 73.19%; H, 8.91%.

Example 8
Synthesis of (2-Oxa-pent-3-enyl)-3-oxatricylo [3.2.0$^{2,3}$] hept-5-ene (NEP)

A procedure analogous to that employed for CP was used to synthesize NEP. Complete disappearance of the bands assigned to the allyl groups (δ ppm 5.0–5.4, CH$_2$=; 5.8–6.1, CH=; 3.8–4.1, CH$_2$) occurred after 4 h. A yield of 94% of pure NEP (cis/trans ~58:32) was obtained after purification by fractional vacuum distillation. The compound had a boiling point of 160° C./15 mm Hg.

$^1$H NMR (CDCl$_3$): δ (ppm) 0.7–0.9 (H$_{6n}$, 1H); 1.0–1.3 (H$_{7anti}$, 1H); 1.3–1.4 (H$_{7syn}$, 1H); 1.4–1.6 (H$_{11}$, 3H); 1.65–1.95 (H$_{6X}$, 1H); 2.2–2.4 (H$_5$, 1H); 2.4–2.6 (H$_1$+H$_4$, 2H); 3.0–3.3 (H$_2$+H$_3$, 2H); 3.4–3.8 (H$_8$, 4H); 4.3–4.5 (H$_{10}$); 4.65–4.85 (H$_{10E}$); 5.8–6.0 (H$_{9Z}$); 6.1–6.3 (H$_{9E}$,)

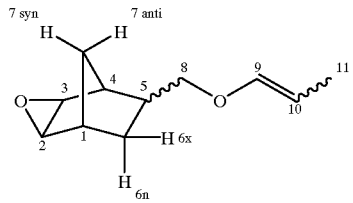

Elemental Analysis. Calculated for C$_{11}$H$_{16}$O$_2$: C, 73.30%; H, 8.95%. Found: C, 73.08%; H, 8.88%.

Example 9
Synthesis of 1(2-Oxapentyl)-6-methylcyclohex-3-ene (MCPr)

A procedure analogous to CA (Method A) was used to synthesize MCPr. A yield of 88% was obtained. The compound had a boiling point of 31° C. at 0.1 mm Hg.

$^1$H NMR (CDCl$_3$): δ (ppm) 0.7–1.0 (H$_{11}$+H$_7$, 6H); 1.5–1.9 (H$_2$+H$_5$+H$_6$, 6H); 1.9–2.3 (H$_1$+H$_{10}$, 3H); 3.2–3.6 (H$_8$+H$_9$, 4H); 5.5–5.8 (H$_3$+H$_4$, 2H).

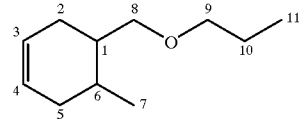

Elemental Analysis. Calculated for C$_{11}$H$_{20}$O: C, 78.58%; H, 11.98%. Found: C, 78.49%; H, 11.88%.

Synthesis of 1(2-Oxa-pentyl)-6-methyl-3,4-epoxycyclohexane (MCEPr)

An epoxidation procedure analogous to CEA was used to synthesize MCEPr. A yield of 70% was obtained. The compound had a boiling point of 45° C. at 0.25 mm Hg.

$^1$H NMR (CDCl$_3$): δ (ppm) 0.7–1.0 (H$_{11}$+H$_7$, 6H); 1.1–1.7 (H$_2$+H$_5$+H$_6$, 6H); 1.7–2.3 (H$_1$+H$_{10}$, 3H); 3.0–3.2 (H$_3$+H$_4$, 2H); 3.2–3.6 (H$_8$+H$_9$, 4H).

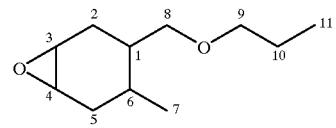

Elemental Analysis. Calculated for C$_{11}$H$_{20}$O$_2$: C, 71.7%; H, 10.94%. Found: C, 71.57%; H, 10.92%

Example 10
Preparation of 2(3'-Oxahex-5'-ene)-6,6-dimethyl-8-oxatricyclo [3.1.1.1$^{2,3}$] octane (Allyl Nopol Ether, II)

A 500 mL round bottom flask equipped with a water condenser, magnetic stirrer, nitrogen inlet and thermometer was charged with nopol ((R)-(-)-2-(2'-hydroxymethyl)-6,6-dimethyl-8-oxatricyclo [3,1,1,1$^{2,3}$]octane] (49.88 g, 0.300 mol), sodium hydride (80%, 14.01 g, 0.4545 mol) and THF (200 mL). Nopol is a chiral terpene derivative prepared from β-pinene by condensation with formaldehyde. This mixture was heated to 60° C. for 30 min, then cooled to room temperature. Allyl bromide (36.66 g, 0.300 mol) was added dropwise within 1 h and then stirred at 60° C. for another 3 h. The resulting cooled reaction mixture was washed with three portions of 50 mL brine and the organic layer separated and dried over anhydrous sodium sulfate. After evaporation of solvents using a rotary evaporator, one third of the residue was purified by flash chromatography (silica gel, 1:19 ethyl acetate:hexane) to give allyl nopol ether (II) (15.02 g, 95.0% yield based on nopol). TLC R$_f$=0.71 (1:9 ethyl acetate:hexane).

$^1$H NMR (CDCl$_3$, 500 MHZ): δ (ppm) 5.92 (m, H$_{5'}$, 1H); 5.27 (m, H$_3$, 1H); 5.22 (dd, H$_{6'}$, 2H); 3.97 (d, H$_{4'}$, 2H); 3.45 (t, H$_{2'}$, 2H); 2–2.4 (m, H$_{1,1',2,4,5,7}$, 7H); 1.26 (s, H$_8$, 3H); 11.16 (d, H$_7$, 1H); 0.83 (s, H$_9$, 3H).

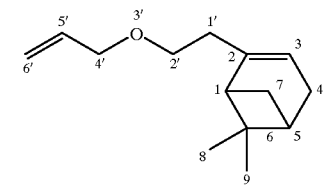

Example 11
Preparation of 2(3'-Oxahex-5'-ene)-6,6-dimethyl-8-oxatricyclo [3.1.1.1$^{2,3}$] octane (Allyl Nopol Ether Epoxide, III)

Into a 2 L three-necked round-bottom flask fitted with an efficient mechanical stirrer, a Claisen condenser, two addition funnels and a pH meter were placed allyl nopol ether (II) (10.81 g, 0.0524 mol), methylene chloride (50 mL), acetone (40 mL), phosphate buffer (pH=7.4, 200 mL) and 18-crown-6 ether (0.4 g). The flask was cooled to 5° C. using an ice bath. Then, Oxone® (2KHSO$_5$, K$_2$SO$_4$, KHSO$_4$; 39.80 g) as a 1 M aqueous solution was added dropwise within 1 h. At the same time, potassium hydroxide (13.75 g) in 100 mL water was also slowly added to neutralize the acid and keep the pH between 7.1 and 7.5. Upon the completion of the addition of Oxone®, the reaction mixture was stirred at 50° C. for an additional 4 h. The resulting mixture was filtered, extracted with three 50 mL aliquots of dichloromethane, and the combined organic layers were washed with brine and dried over anhydrous magnesium sulfate. Flash chromatography (silica gel, 1:19 ethyl acetate:hexane) gave III (11.12 g, 95.6% yield); TLC R$_f$=0.21 (1:19 ethyl acetate:hexane).

$^1$H NMR (CDCl$_3$, 500 MHZ): δ (ppm) 5.90 (m, H$_{5'}$, 1H); 5.22 (dd, H$_{6'}$, 2H); 3.96 (m, H$_{4'}$, 2H); 3.50 (m, H$_{2'}$, 2H); 3.17 (d, H$_3$, 1H); 2.1–1.6 (m, H$_{1,1',2,4,5,7}$, 9H); 1.50 (S, H$_9$, 3H); 0.97 (s, H$_{10}$, 3H).

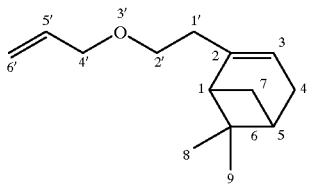

Elemental Analysis: Calcd. for C$_{14}$H$_{22}$O$_2$: C, 75.63%; H, 97%. Found: C, 75.77%; H, 9.90%.

Example 12

Preparation of 2(3'-Oxahex-4'-ene)-6,6-dimethyl-8-oxatricyclo [3.1.1.1$^{2,3}$] octane (Nopol 1-Propenyl Ether Epoxide, IV)

A 25 mL round bottom flask equipped with a magnetic stirrer, a thermometer and a water condenser was charged with tris(triphenylphosphine)ruthenium(II) dichloride (0.0191 g, 0.0199 mmol). The reaction mixture was heated to 120° C., then III (4.44 g, 20.0 mmol) was added. At this time, a nitrogen flow into the reaction flask was started. The reaction mixture was heated at 120° C. for 1.5 h. Monitoring the reaction mixture by TLC showed that virtually all the starting material had reacted. Reaction was continued for an additional 1h and then cooled to room temperature. Flash chromatography (silica gel, 1:9 ethyl acetate:hexane) gave IV (4.31 g, yield: 97.1%). TLC R$_f$=0.38 (1:19 ethyl acetate:hexane) as a mixture of E and Z 1-propenyl ether isomers.

$^1$H NMR (CDCl$_3$, 500 MHZ): δ (ppm) [6.19 (dd, H$_{4'E}$), 5.91 (dd, H$_{4'Z}$) (1H)]; [4.76 (m, H$_{5'E}$), 4.38 (m, H$_{5'Z}$) (1H)]; 3.77, 3.68 (m H$_{2'}$, 2H); 3.22, 3.16 (dd, H$_3$, 1H); 2.10–1.5 (m, H$_{1,1',2,4,5,7}$, 9H); 1.55 (t, H$_6$, 3H); 1.30 (s, H$_9$, 3H); 0.97 (d, H$_{10}$, 3H).

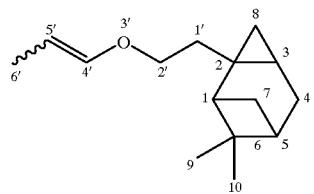

Elemental Analysis: Calcd. for C$_{14}$H$_{22}$O$_2$: C, 75.63%; H, 19.97%. Found: C, 75.58%; H, 9.93%.

Example 13

Preparation of 2(3'-oxabutane)-6,6-dimethyl-8-oxatricyclo [3.1.1.1$^{2,3}$]octane (Nopol Methyl Ether Epoxide, V)

V was prepared by the methylation of nopol with methyl iodide followed by epoxidation using methods similar to those employed for II and III described above. Flash chromatography (silica gel, 1:4 ethyl acetate: hexane) gave pure V (92.6% total yield for two steps); TLC R$_f$=2.9 (1:9 ethyl acetate:hexane) as a colorless oil.

$^1$H NMR (CDCl$_3$, 500 MHZ): δ (ppm) 3.43 (m, H$_{2'}$, 2H); 3.31 (s, H$_{4'}$, 3H); 3.16 (d, H$_3$, 2H); 1.6–2.1 (m, H$_{1,1',2,4,5,7}$, 9H); 1.50 (s, H$_9$, 3H); 0.96 (s, H$_{10}$, 3H).

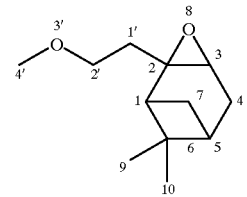

Elemental Analysis: Calcd. for C$_{12}$H$_{18}$O$_2$: C, 73.43%; H, 10.27%. Found: C, 73.48%; H, 10.16%.

Polymerization Studies

Polymerizations of all the monomers were monitored using real-time infrared spectroscopy (RTIR). A Midac M-1300 FTIR spectrometer equipped with a liquid nitrogen cooled MCT detector was used. The instrument was fitted with a UVEXS Model SCU-110 mercury arc lamp equipped with a flexible liquid optic wand. The end of this wand was placed at a distance of 5 cm and directed at an incident angle of 45° onto the sample window. The UV light intensity was measured with the aid of an International Light Co. Control-Cure Radiometer at the sample window and was found to be 2200 mJ/cm$^2$ min (36.7 mW/cm$^2$).

Photopolymerizations were carried out at room temperature in bulk monomers containing 1 mol % IOC11 (4-n-undecyloxyphenyl)phenyliodonium hexafluoroantimonate) or IOC10(4-n-decyloxyphenyl)phenyliodonium hexafluoroantimonate) as the photoinitiator. IOC11 was very soluble in CEA, CEP, MCEA and MCEP. For CP and MCP the monomer/photoinitiator mixture was heated at 50° C. in a water bath for 10 minutes to achieve dissolution. The monomer/photoinitiator solutions were coated onto a 30 mm polypropylene film, covered with another polypropylene film, and then mounted in a 5 cm×5 cm slide frame. Infrared spectra were collected at a rate of 0.5–3 spectra per second using a LabCalc, data acquisition software obtained from the Galactic Corp. and were processed using GRAMS-386 software from the same company. During irradiation, the decrease of the absorbance due to the 1-propenyl ether double bond centered at 1667 cm$^{-1}$ and the decrease of the absorbance due to the epoxy group between 780–810 cm$^{-1}$ were monitored. In all cases, experiments were performed in triplicate to verify reproducibility.

Photoinitiated Cationic Polymerization of Hybrid Monomers

The cationic polymerization of the monomers prepared as described in Examples 1–9 containing two highly reactive cationically polymerizable groups is inherently difficult to follow by conventional methods. This is not only due to the fact that the polymerizations are exceedingly rapid, but also because the polymers which are formed are crosslinked. When typical initiators such as Lewis and Brønsted acids are added to these monomers, gel formation sets in even before the catalysts can be homogeneously dispersed in the reaction mixture. The above difficulties can be offset through the use of latent onium salt photoinitiators such as diaryliodonium salts. Polymerizations can be induced on demand through the irradiation of the monomer-photoinitiator mixtures with ultraviolet light. In the following examples IOC11 was used as the photoinitiator. IOC11 exhibits high solubility in a wide variety of polar and non-polar monomers. The enhanced solubility is provided both by the unsymmetrical structure of the photoinitiator as well as by the long alkoxy chains containing an odd number of carbon atoms. UV irradiation at the $\lambda_{max}$ (247 nm) of this salt results in facile photolytic decomposition with a high quantum yield $\Phi = \sim 0.7$).

The cationic photopolymerization of the monomers synthesized in Examples 1–9 was studied using Fourier transform real-time infrared spectroscopy (RTIR). This technique involves monitoring the decrease of the characteristic absorption of a functional group undergoing polymerization as a function of time. Since the integrated areas of the above mentioned absorptions are directly proportional to the conversions at any given time, one directly obtains plots of the reaction profiles. The initial slopes of these curves are proportional to the rates of polymerization, and using this data, the extents of reaction can be calculated. Typically, the conversions increase with time until a maximum value referred to as the limiting conversion is reached.

Photopolymerizations of CP, CEA and CEP

The RTIR conversion versus time curves for the independent photoinitiated cationic polymerizations of the epoxy monomer CEA and 1-propenyl ether monomer CP are shown in FIG. 1. Each kinetic run was carried out at 25° C. in triplicate and the resulting conversion versus time curves show a reproducibility of ±5%. A comparison of the two curves shows that the polymerizations of both epoxy and 1-propenyl ether functional groups of these two monomers proceeds to very high conversions. However as expected, the polymerization of the 1-propenyl ether group is considerably faster than that of the epoxy group.

Figure 2:
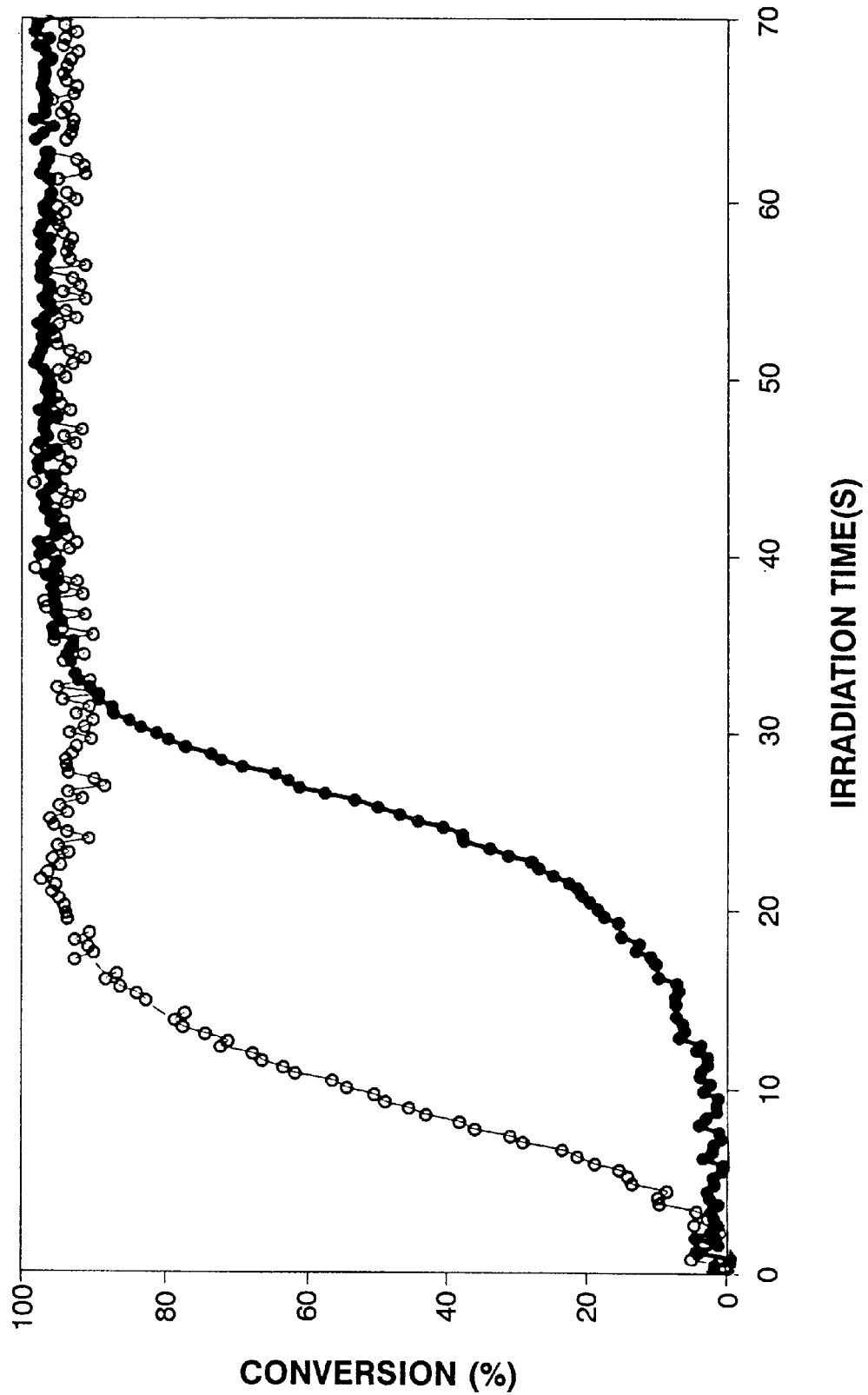

In a second study depicted in FIG. 2, there is shown the simultaneous polymerization of a 1:1 molar mixture of the model compounds CEA and CP. In contrast to the previous results and unexpectedly, the polymerizations of the epoxide and the 1-propenyl ether groups in the mixture take place at nearly the same rates as indicated by the slopes of the curves. Both polymerizations proceed to very high (>95%) conversions. However, it may also be noted that first, surprisingly the polymerization of the epoxycyclohexyl groups proceeds faster than that of the 1-propenyl ether groups, and second, the polymerization of these latter groups is effectively suppressed until the consumption of the epoxide groups is virtually complete. It may also be observed by comparison with FIG. 1, that the rate of polymerization of the epoxy group of CP in the mixture is accelerated in the presence of the 1-propenyl ether.

Figure 3:
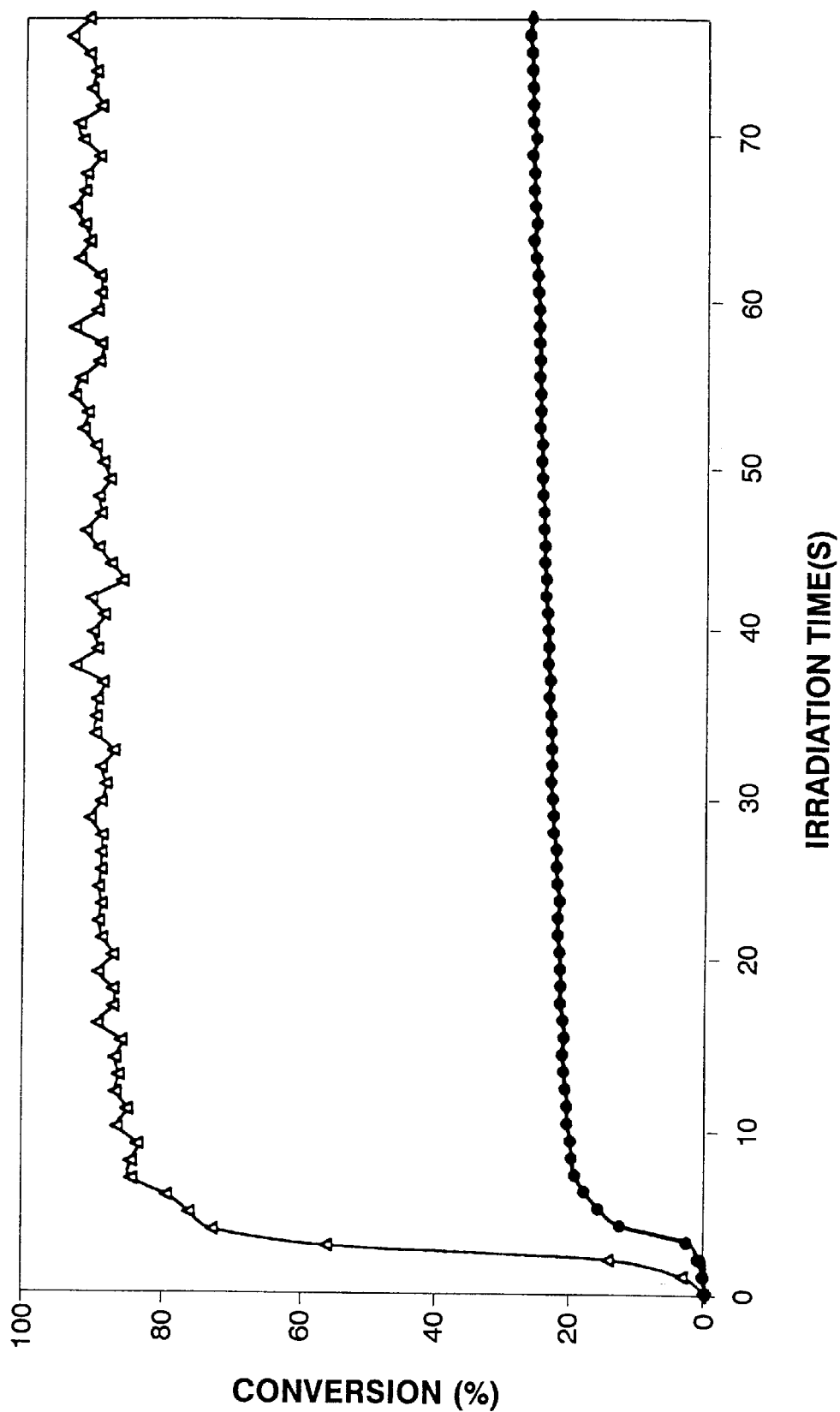

The RTIR conversion versus time curves for the photo-initiated cationic polymerization of the epoxy and 1-propenyl ether groups of the hybrid monomer CEP are shown in FIG. 3. Inspection of the curves shows that the polymerizations of the epoxycyclohexyl groups are very rapid and that these moieties undergo a more rapid reaction than the 1-propenyl ether groups. In addition, the conversion of the epoxy functional groups reaches 95%, while in the case of the 1-propenyl ether groups, the ultimate conversion is only about 35%. Therefore, it appears that the epoxide polymerization undergoes a dramatic acceleration due to the presence of the 1-propenyl ether group in the same molecule. The acceleration effect of the epoxide polymerization in CEP is even more pronounced than in the 1:1 molar mixture of model compounds CEA and CP.

Photopolymerizations of MCP, MCEA and MCEP

Figure 4:
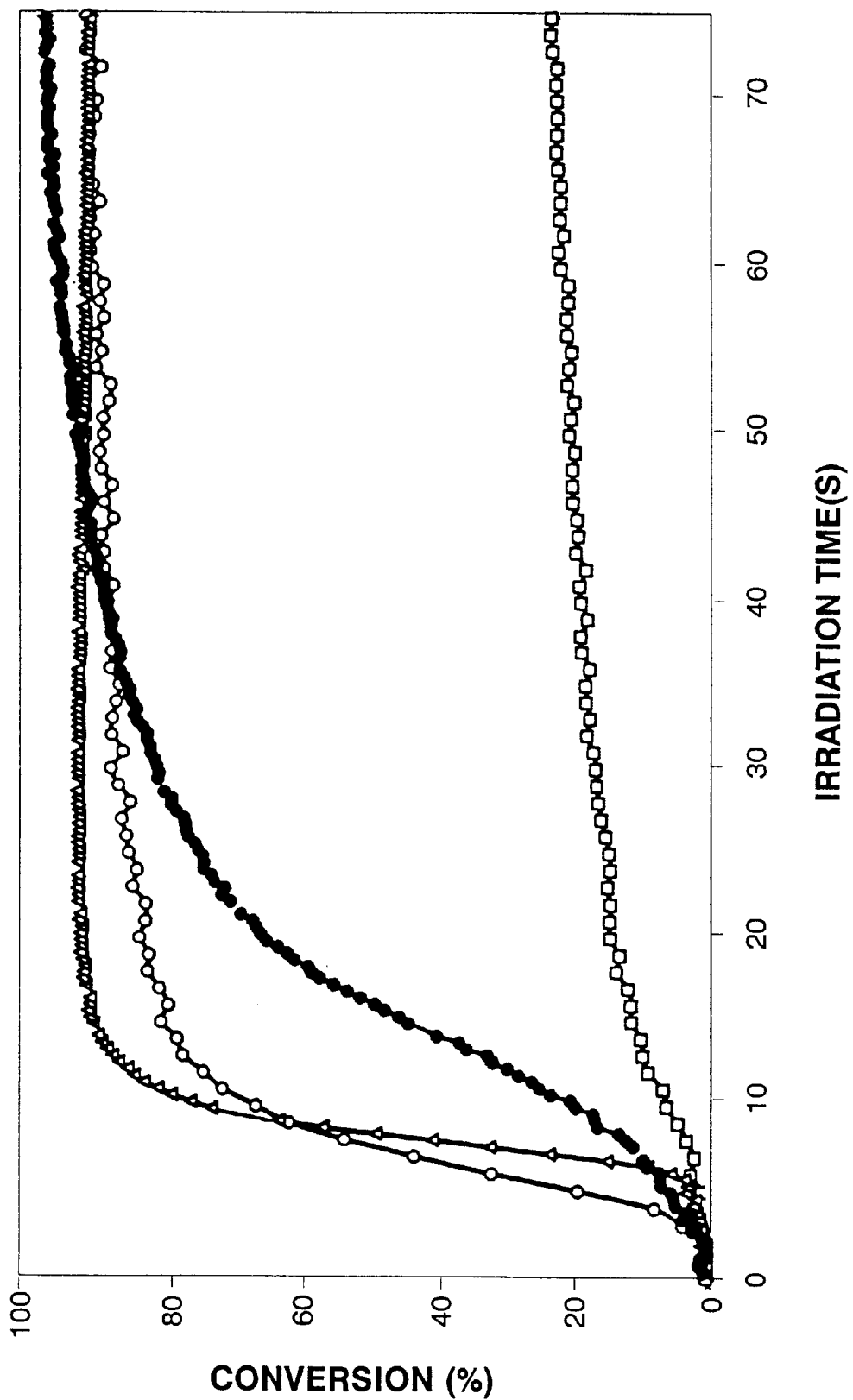
Figure 5:
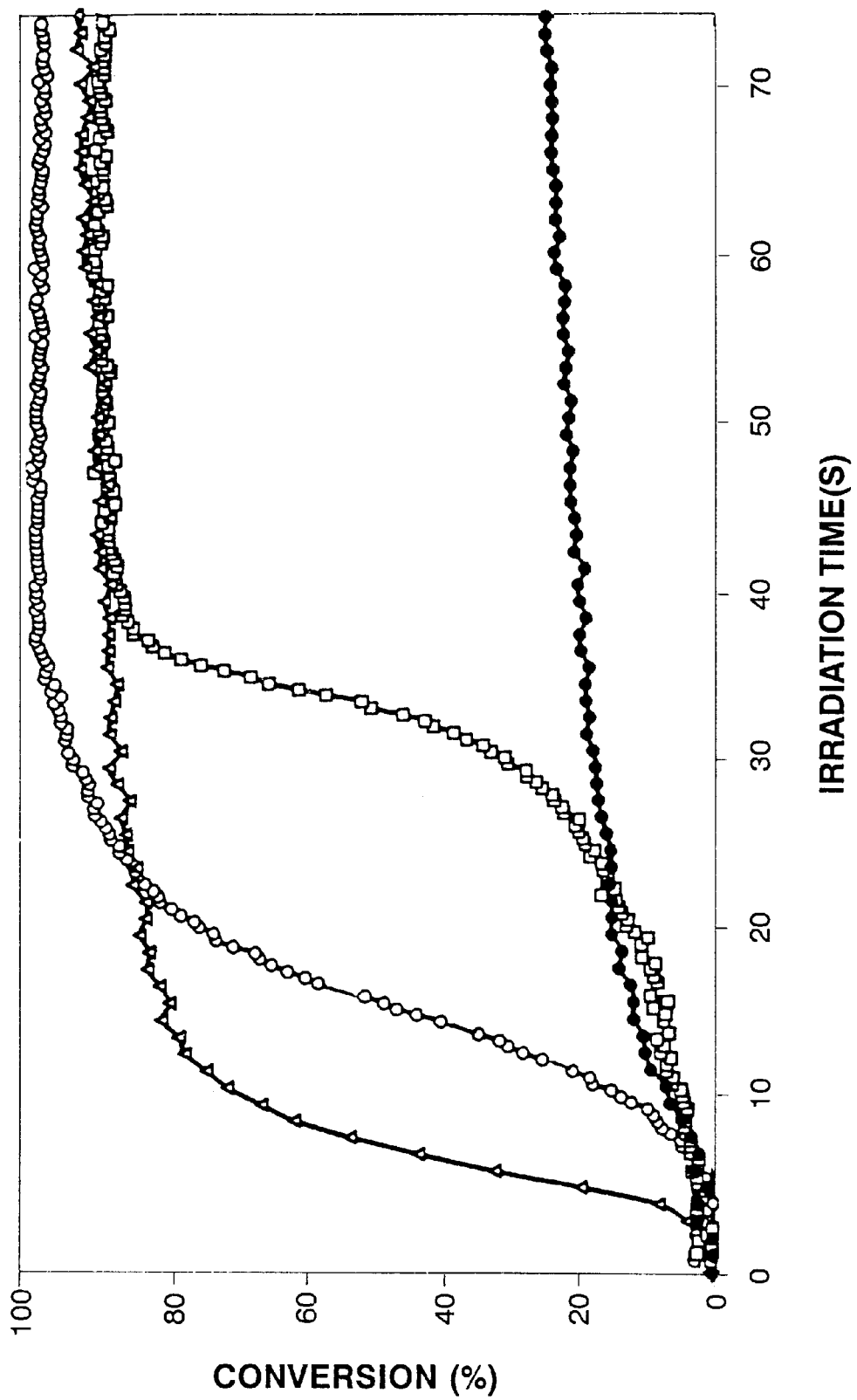

Identical observations were made for the photoinitiated cationic polymerization of MCEP as were found for CEP. In FIG. 4 is depicted the RTIR curves obtained for the polymerization of the epoxide and 1-propenyl ether groups in this hybrid monomer. These curves are presented for comparison in the same figure together with the individual model compound polymerizations of the epoxide groups in MCEA and the 1-propenyl ether groups in MCP. Again, a marked acceleration of the polymerization of the epoxycyclohexyl groups and a deceleration of the 1-propenyl ether moieties of MCEP takes place. In effect, the reactivity of the epoxide group in MCEP resembles that of an independent 1-propenyl ether group. It may also be noted that not only is the rate of the 1-propenyl ether polymerization suppressed, but so also is the conversion. FIG. 5 presents the curves obtained when the photopolymerization of MCEA and MCP are carried out in a 1:1 molar mixture. The curves for the polymerization of MCEP are again superimposed on these two latter curves for comparison. When the equimolar mixture of MCEA and MCP is polymerized, the rate of the epoxide monomer polymerization is accelerated and the 1-propenyl ether monomer is depressed. Comparison of these model compound polymerizations with MCEP again indicates that the rate of the epoxide polymerization in MCEP is unexpectedly high. To account for these results, it must be concluded from the study of this monomer as well as that of CEP that there must be an appreciable amount of intramolecular reaction between the two different functional groups in the same molecule which gives rise to a very rapid crossover reaction from 1-propenyl ether polymerization to ring-opening epoxide polymerization.

Photopolymerizations of NP, NAE and NEP

Figure 6:
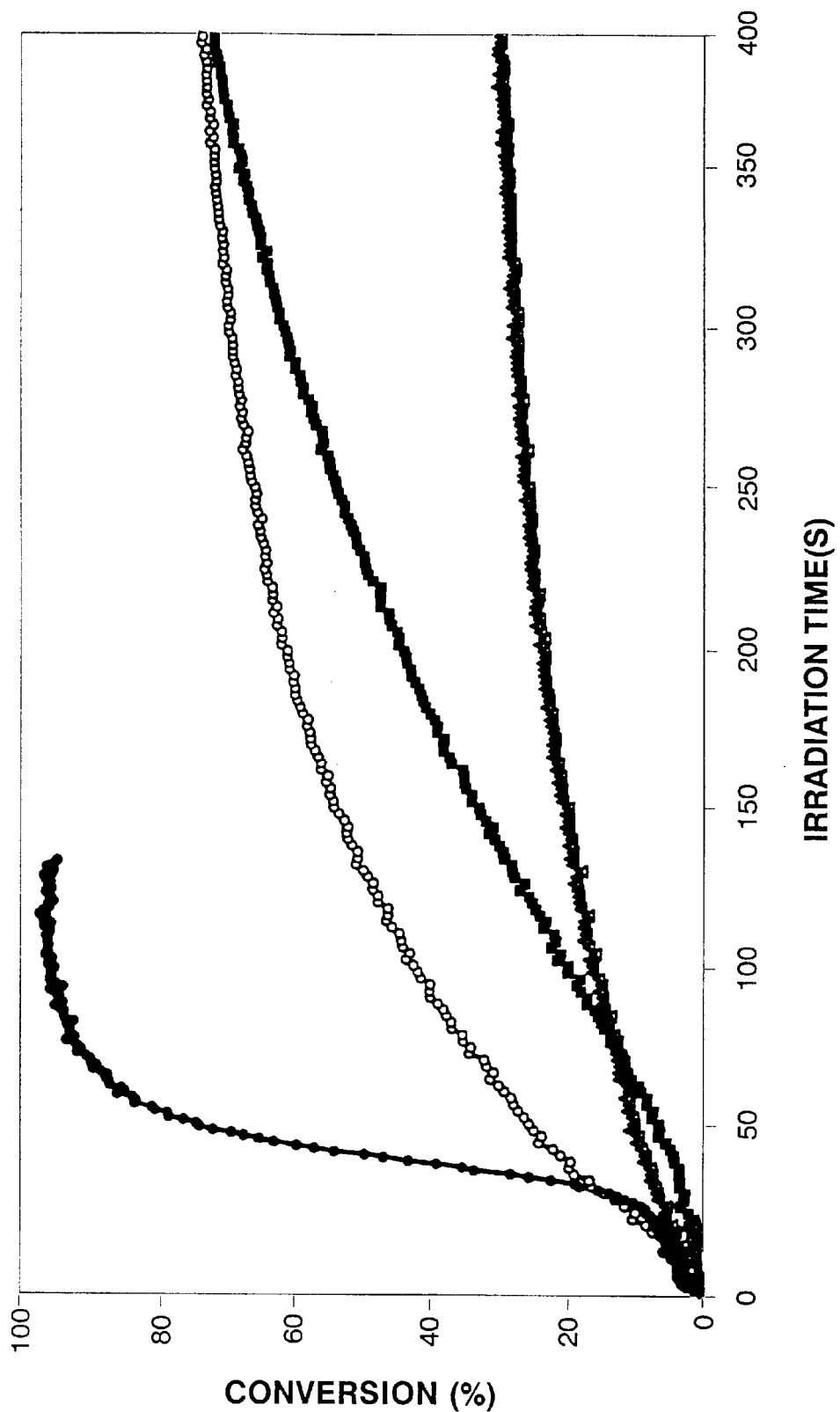

Shown in FIG. 6 is a series of RTIR curves for the photopolymerization of the hybrid epoxy 1-propenyl ether monomer NEP and several related model compounds. The photoinitiated cationic ring-opening epoxide polymerization of NEP is slower than either CEP or MCEP, however, like these latter two monomers it is more rapid than the 1-propenyl ether group in the same molecule. The comparatively slow epoxide polymerization of NEP is due to the steric hindrance provided by the bicyclic norbornenyl ring and this effect has been observed previously. Also shown for comparison in FIG. 6 are the epoxide polymerization of the epoxide group of the isomeric allyl ether compound and precursor NEA as well as the 1-propenyl ether NP. Very rapid polymerization of the sterically hindered 1-propenyl ether of NP takes place while polymerization of the epoxide group of NAE is slower than that of NEP.

The outstanding reactivities of hybrid monomers CEP and MCEP were further demonstrated in a practical manner by spreading them as thin films containing 0.5 mol % IOC11 onto a steel substrate and then irradiating them in a 300 W Fusion Systems Laboratory UV Cure System. Using this apparatus, equipped with a conveyor, the speed with which crosslinking takes place can be estimated. Both CEP and MCEP were fully crosslinked at the highest speed of the conveyor (46 m/min, 150 ft/min) while NEP required two exposures at this speed for conversion to a tack-free film.

Thermal Properties

The polymers prepared by the cationic photoinitiated polymerizations of the monomers of the present invention exhibit glass transition temperatures ($T_g$) as measured by DSC which are quite high, as seen in the following Table:

| Polymerized Monomer | Glass Transition Temperature |
|---|---|
| CEP | 176° C. |
| MCEP | 174° C. |
| NEP | 141° C. |
| | (measured at 5° C./min in air) |

Cationic Photopolymerization Studies

The cationic photopolymerizations of IV and the other monomers prepared in Examples 10–13 were studied using real-time infrared spectroscopy (RTIR). The photopolymerization studies were conducted using the cationic photoinitiator IOC10 at a concentration of 0.5 mol % per functional group present. Thus, in the case of the monomer IV, 1.0 mol % was used due to presence of the two different polymerizable functional groups. The monomers were coated onto a polyethylene film and irradiated with UV light at room temperature. Simultaneously, the conversions of each functional group to polymer were monitored by following the decrease in the intensity of either the 870 cm$^{-1}$ (epoxy) or the 1668 cm$^{-1}$ (1-propenyl ether) infrared absorption band upon UV exposure as a function of time. Since monomer IV was found to be highly reactive, it was found necessary to adjust the light intensity to a very low level (256 mJ/cm$^2$min, 4.3 mW/cm$^2$) to slow the polymerization sufficiently to allow data acquisition.

Figure 7:
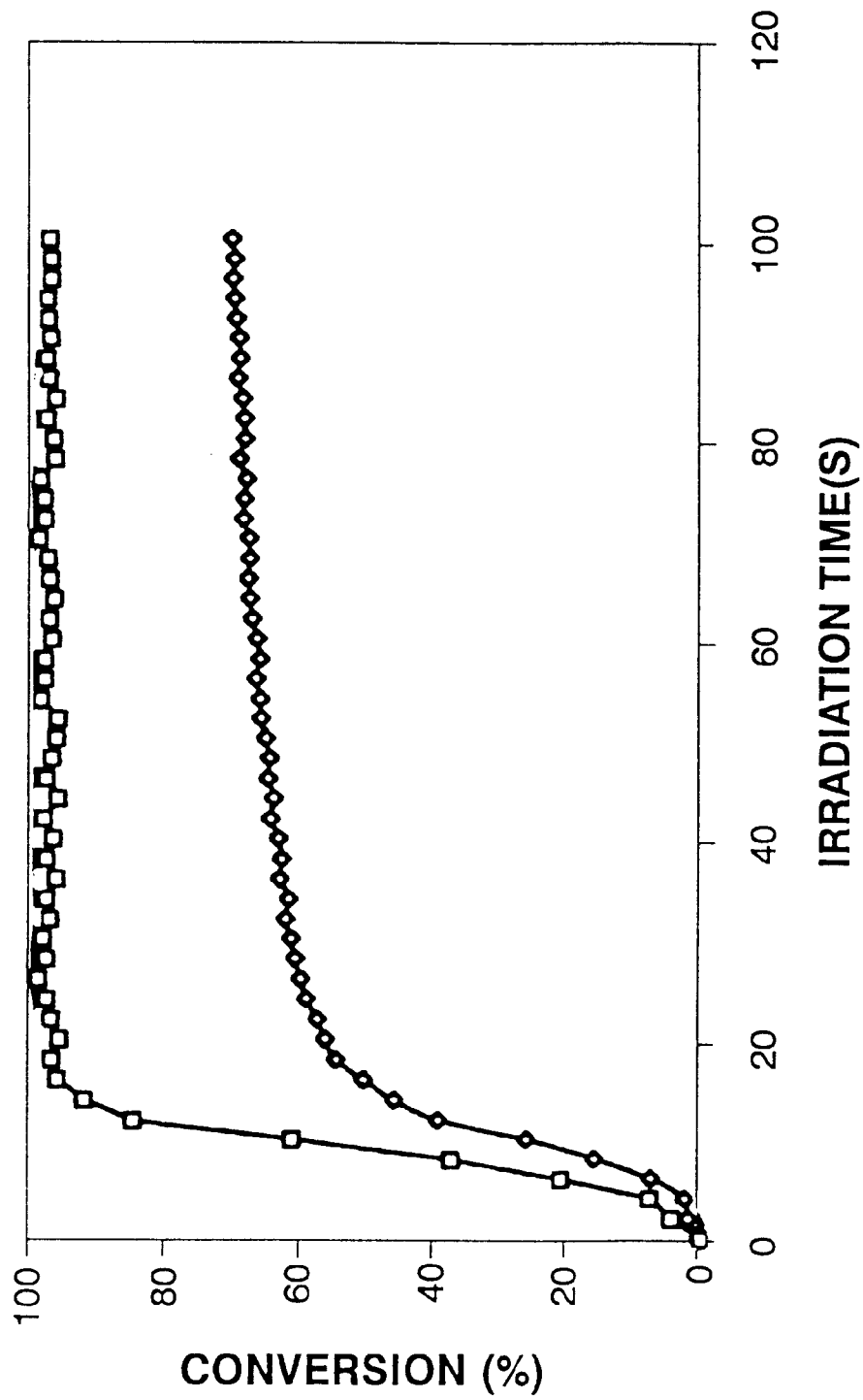

The RTIR curves for the cationic photopolymerization of IV are shown in FIG. 7. A comparison of the curves in FIG. 7 for monomer IV shows that the rate of polymerization of the epoxy group as indicated by the slope of the initial portion of the RTIR curve is considerably higher than that of the 1-propenyl ether group. While the cationic vinyl polymerizations of enol ether monomers in general and 1-propenyl ether monomers[1] in particular are much more rapid than the most reactive epoxide ring-opening polymerization reactions and are among the most rapid polymerizations known, here, the situation is surprisingly reversed.

Captions for Figures

FIG. 1. Study of the independent photoinitiated cationic polymerizations of CP (■), (1-propenyl ether) and CEA (●), (epoxide).

FIG. 2. Study of the photoinitiated cationic polymerizations of a 1:1 mixture of CP (●), (1-propenyl ether) and CEA (○), (epoxide).

FIG. 3. RTIR study of the photoinitiated cationic polymerization of CEP in the presence of 1 mol % IOC-11. (Δ), epoxide; (●); 1-propenyl ether.

FIG. 4. RTIR comparison of the photoinitiated cationic polymerizations of MCEP, MCP and MCEA. MCP (Δ), (1-propenyl ether) and MCEA (●) (epoxide); MCEP (○), (epoxide); MCEP (□) (1-propenyl ether).

FIG. 5. RTIR comparison of the photoinitiated cationic polymerization of a 1:1 mixture of MCP (□), (1-propenyl ether) and MCEA (○), (epoxide); MCEP (Δ), epoxide; MCEP (●), (1-propenyl ether).

FIG. 6. RTIR study of the polymerizations of NEP (○), (epoxide), (■), (1-propenyl ether); NP (●), (1-propenyl ether); NEA (Δ), (epoxide).

FIG. 7. RTIR study of the cationic photopolymerization of IV. □, epoxy groups (870 cm$^{-1}$); ◊, 1-propenyl ether groups (1668 cm$^{-1}$).

What is claimed is:

1. A compound which (A) contains 1 to 3 cycloaliphatic epoxy groups and an oxidizable group containing an ether linkage or ethylenic or acetylenic bond; and (B) undergoes photopolymerization when exposed to ultraviolet, electron beam or X-ray irradiation in the presence of a photoinitiator.

2. A compound of formula (1), (2), (3) or (4)

(1)

(2)

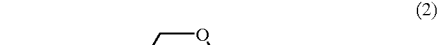

(3)

(4)

wherein i is 1, 2, or 3;

$R^b$ is hydrogen or straight or branched alkyl containing 1 to 20 carbon atoms;

$R^c$ is hydrogen or straight or branched alkyl containing 1 to 20 carbon atoms;

$R^e$ is a single bond or straight or branched divalent alkyl containing 1 to 20 carbon atoms;

a is 0 or 1, and f is 0 or 1;

Y is hydrogen or straight or branched alkyl containing up to 12 carbon atoms;

one of L and M is —CH$_2$— and the other is a single bond;

when i is 1, AG is —OM or a monovalent heterocyclic group containing 3, 4 or 5 carbon atoms and 1 or 2 oxygen atoms, wherein M is straight or branched alkyl containing 2 to 20 carbon atoms which contains a C═C bond, a C≡C bond, or an ether oxygen, or M is phenyl, benzyl, or a monovalent heterocyclic group containing 3, 4 or 5 carbon atoms and 1 or 2 oxygen atoms, and AG is optionally substituted with an R group;

when i is 2, AG is —O—D—O— wherein D is divalent straight or branched alkyl containing up to 20 carbon atoms which optionally contains a C═C bond or a C≡C bond, and which is optionally substituted with an R group, wherein D can optionally be interrupted with an ether oxygen, $C_6H_4$ phenylene, or cycloalkyl containing 2 to 20 carbon atoms and 0–2 oxygen atoms;

when i is 3, AG is —O—T(—O—)—O—, wherein T is trivalent straight or branched alkyl containing up to 25 carbon atoms which optionally contains a C═C bond or a C≡C bond, wherein T can optionally be interrupted with an ether oxygen; or T is a cycloalkyl group of 3 to 25 carbon atoms or a phenyl group and is substituted with 3 groups each independently having the formula $C_tH_{2t}$ wherein t is 1 to 20;

R is phenyl optionally substituted with a G group, or cycloalkyl or cycloalkyl-alkyl containing 5 to 25 carbon atoms wherein up to 2 ring carbon atoms are replaced with oxygen atoms, and R is optionally substituted with a G group; and G is alkyl containing 1 to 20 carbon atoms, —CHO, alkoxy containing 1 to 20 carbon atoms, cycloalkoxy or cycloalkyl containing 5 to 25 carbon atoms, —COOH, —$NO_2$, phenyl, halo, or vinyl.

3. A compound according to claim 2 having formula (1).

4. A compound according to claim 3 wherein i is 1.

5. A compound according to claim 4 wherein f is 0 and a is 0.

6. A compound according to claim 5 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, $R^e$ is a chemical bond or alkyl containing 1 to 6 carbon atoms, and AG is selected from the group consisting of tetrahydrofuryl, tetrahydrofurfuryl, dioxolanyl, oxanyl, and groups of the formula —OM wherein M is phenyl, benzyl, tetrahydrofuryl, dioxolanyl, tetrahydrofurfuryl, oxanyl, or straight or branched alkyl which contains 2 to 6 carbon atoms and a double or triple bond or an ether oxygen and which is optionally substituted with phenyl.

7. A compound according to claim 4 wherein f is 0 and a is 1.

8. A compound according to claim 7 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, $R^e$ is a chemical bond or alkyl containing 1 to 6 carbon atoms, and AG is selected from the group consisting of tetrahydrofuryl, tetrahydrofurfuryl, dioxolanyl, oxanyl, and groups of the formula —OM wherein M is phenyl, benzyl, tetrahydrofuryl, dioxolanyl, tetrahydrofurfuryl, oxanyl, or straight or branched alkyl which contains 2 to 6 carbon atoms and a double or triple bond or an ether oxygen and which is optionally substituted with phenyl.

9. A compound according to claim 8 wherein AG is allyloxy, 1-propenyloxy, benzyloxy, oxanyloxy, vinyloxy, phenoxymethoxy, phenoxyethoxy, methoxymethoxy, ethoxymethoxy, tetrahydrofuryloxy, methoxybenzyloxy, dioxolanyl, methoxyethyl, —$CH_2$═CH, chlorobenzyloxy, benzyloxyethoxy, —$OCH_2CH$═$CHC_6H_5$, or —$OCH_2CH$═$CHCH_3$.

10. A compound according to claim 4 wherein f is 1 and a is 0.

11. A compound according to claim 10 wherein AG is allyloxy, 1-propenyloxy, benzyloxy, oxanyloxy, vinyloxy, phenoxymethoxy, phenoxyethoxy, methoxymethoxy, ethoxymethoxy, tetrahydrofuryloxy, methoxybenzyloxy, dioxolanyl, methoxyethyl, —$CH_2$═CH, chlorobenzyloxy, benzyloxyethoxy, —$OCH_2CH$═$CHC_6H_5$, or —$OCH_2CH$═$CHCH_3$.

12. A compound according to claim 4 wherein f is 1 and a is 1.

13. A compound according to claim 12 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, and $R^e$ is a chemical bond or alkyl containing 1 to 6 carbon atoms.

14. A compound according to claim 12 wherein AG is allyloxy, 1-propenyloxy, benzyloxy, oxanyloxy, vinyloxy, phenoxymethoxy, phenoxyethoxy, methoxymethoxy, ethoxymethoxy, tetrahydrofuryloxy, methoxybenzyloxy, dioxolanyl, methoxyethyl, —$CH_2$═CH, chlorobenzyloxy, benzyloxyethoxy, —$OCH_2CH$═$CHC_6H_5$, or —$OCH_2CH$═$CHCH_3$.

15. A compound according to claim 3 wherein i is 2.

16. A compound according to claim 15 wherein f is 0 and a is 0.

17. A compound according to claim 16 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, and $R^e$ is a chemical bond or alkyl containing 1 to 6 carbon atoms.

18. A compound according to claim 16 wherein AG is —$OCH_2CH$≡$CHCH_2O$—, —$OCH_2C_6H_4CH_2O$—, —$OCH(C_6H_5)O$—, —$OCH_2O$—, or —$OCH_2CH$═$CHCH_2O$—.

19. A compound according to claim 15 wherein f is 0 and a is 1.

20. A compound according to claim 19 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, and $R^e$ is a chemical bond or alkyl containing 1 to 6 carbon atoms.

21. A compound according to claim 20 wherein $R^e$ is a chemical bond, —$C(CH_3)_2$— or —$CH_2$—.

22. A compound according to claim 19 wherein AG is divalent alkyl containing 1 to 6 carbon atoms, is optionally interrupted with an ether oxygen, is optionally interrupted by or substituted with phenyl, and optionally contains a double or triple bond.

23. A compound according to claim 22 wherein AG is —$OCH_2CH$≡$CHCH_2O$—, —$OCH_2C_6H_4CH_2O$—, —$OCH(C_6H_5)O$—, —$OCH_2O$—, or —$OCH_2CH$═$CHCH_2O$—.

24. A compound according to claim 15 wherein f is 1 and a is 0.

25. A compound according to claim 24 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, and $R^e$ is a chemical bond or alkyl containing 1 to 6 carbon atoms.

26. A compound according to claim 24 wherein AG is divalent alkyl containing 1 to 6 carbon atoms, is optionally interrupted with an ether oxygen, is optionally interrupted by or substituted with phenyl, and optionally contains a double or triple bond.

27. A compound according to claim 26 wherein AG is —$OCH_2CH$≡$CHCH_2O$—, —$OCH_2C_6H_4CH_2O$—, —$OCH(C_6H_5)O$—, —$OCH_2O$—, or —$OCH_2CH$═$CHCH_2O$—.

28. A compound according to claim 15 wherein f is 1 and a is 1.

29. A compound according to claim 28 wherein $R^b$ is hydrogen or alkyl containing 1 to 6 carbon atoms, $R^c$ is hydrogen or alkyl containing 1 to 6 carbon atoms, Y is hydrogen or alkyl containing 1 to 6 carbon atoms, and $R^e$ is a chemical bond or alkyl containing 1 to 6 carbon atoms.

30. A compound according to claim 28 wherein AG is divalent alkyl containing 1 to 6 carbon atoms, is optionally interrupted with an ether oxygen, is optionally interrupted by or substituted with phenyl, and optionally contains a double or triple bond.

31. A compound according to claim 30 wherein AG is —OCH$_2$CH≡CHCH$_2$O—, —OCH$_2$C$_6$H$_4$CH$_2$O—, —OCH(C$_6$H$_5$)O—, —OCH$_2$O—, or —OCH$_2$CH=CHCH$_2$O—.

32. A compound according to claim 3 wherein i is 3.

33. A compound according to claim 32 wherein f is 0 and a is 0.

34. A compound according to claim 33 wherein R$^b$ is hydrogen or alkyl containing 1 to 6 carbon atoms, R$^c$ is hydrogen or alkyl containing 1 to 6 carbon atoms, Y is hydrogen or alkyl containing 1 to 6 carbon atoms, and R$^e$ is a chemical bond or alkyl containing 1 to 6 carbon atoms.

35. A compound according to claim 33 wherein AG is trivalent alkyl containing 1 to 6 carbon atoms, is optionally interrupted with an ether oxygen, is optionally interrupted by or substituted with phenyl, and optionally contains a double or triple bond.

36. A compound according to claim 35 wherein AG is tris(oxymethyl)phenyl.

37. A compound according to claim 32 wherein f is 0 and a is 1.

38. A compound according to claim 37 wherein R$^b$ is hydrogen or alkyl containing 1 to 6 carbon atoms, R$^c$ is hydrogen or alkyl containing 1 to 6 carbon atoms, Y is hydrogen or alkyl containing 1 to 6 carbon atoms, and R$^e$ is a chemical bond or alkyl containing 1 to 6 carbon atoms.

39. A compound according to claim 37 wherein AG is trivalent alkyl containing 1 to 6 carbon atoms, is optionally interrupted with an ether oxygen, is optionally interrupted by or substituted with phenyl, and optionally contains a double or triple bond.

40. A compound according to claim 39 wherein AG is tris(oxymethyl)phenyl.

41. A compound according to claim 32 wherein f is 1 and a is 0.

42. A compound according to claim 41 wherein R$^b$ is hydrogen or alkyl containing 1 to 6 carbon atoms, R$^c$ is hydrogen or alkyl containing 1 to 6 carbon atoms, Y is hydrogen or alkyl containing 1 to 6 carbon atoms, and R$^e$ is a chemical bond or alkyl containing 1 to 6 carbon atoms.

43. A compound according to claim 41 wherein AG is trivalent alkyl containing 1 to 6 carbon atoms, is optionally interrupted with an ether oxygen, is optionally interrupted by or substituted with phenyl, and optionally contains a double or triple bond.

44. A compound according to claim 43 wherein AG is tris(oxymethyl)phenyl.

45. A compound according to claim 32 wherein f is 1 and a is 1.

46. A compound according to claim 45 wherein R$^b$ is hydrogen or alkyl containing 1 to 6 carbon atoms, R$^c$ is hydrogen or alkyl containing 1 to 6 carbon atoms, Y is hydrogen or alkyl containing 1 to 6 carbon atoms, and R$^e$ is a chemical bond or alkyl containing 1 to 6 carbon atoms.

47. A compound according to claim 45 wherein AG is trivalent alkyl containing 1 to 6 carbon atoms, is optionally interrupted with an ether oxygen, is optionally interrupted by or substituted with phenyl, and optionally contains a double or triple bond.

48. A compound according to claim 47 wherein AG is tris(oxymethyl)phenyl.

49. A compound according to claim 2 having formula (2).

50. A compound according to claim 2 having formula (3).

51. A compound according to claim 50 wherein i is 1.

52. A compound according to claim 51 wherein R$^e$ is a chemical bond or alkyl containing 1 to 6 carbon atoms.

53. A compound according to claim 51 wherein AG is selected from the group consisting of tetrahydrofuryl, tetrahydrofurfuryl, dioxolanyl, oxanyl, and groups of the formula —OM wherein M is phenyl, benzyl, tetrahydrofuryl, dioxolanyl, tetrahydrofurfuryl, oxanyl, or straight or branched alkyl which contains 2 to 6 carbon atoms and a double or triple bond or an ether oxygen and which is optionally substituted with phenyl.

54. A compound according to claim 53 wherein AG is allyloxy, 1-propenyloxy, benzyloxy, oxanyloxy, vinyloxy, phenoxymethoxy, phenoxyethoxy, methoxymethoxy, ethoxymethoxy, tetrahydrofuryloxy, methoxybenzyloxy, dioxolanyl, methoxyethyl, —CH$_2$C≡CH, chlorobenzyloxy, benzyloxyethoxy, —OCH$_2$CH=CHC$_6$H$_5$, or —OCH$_2$CH=CHCH$_3$.

55. A compound according to claim 50 wherein i is 2.

56. A compound according to claim 55 wherein R$^e$ is a chemical bond or alkyl containing 1 to 6 carbon atoms.

57. A compound according to claim 55 wherein AG is divalent alkyl containing 1 to 6 carbon atoms, is optionally interrupted with an ether oxygen, is optionally interrupted by or substituted with phenyl, and optionally contains a double or triple bond.

58. A compound according to claim 57 wherein AG is —OCH$_2$CH≡CHCH$_2$O—, —OCH$_2$C$_6$H$_4$CH$_2$O—, —OCH(C$_6$H$_5$)O—, —OCH$_2$O—, or —OCH$_2$CH=CHCH$_2$O—.

59. A compound according to claim 50 wherein i is 3.

60. A compound according to claim 2 having formula (4).

61. A compound according to claim 60 wherein i is 1.

62. A compound according to claim 61 wherein R$^e$ is a chemical bond or alkyl containing 1 to 6 carbon atoms.

63. A compound according to claim 61 wherein AG is selected from the group consisting of tetrahydrofuryl, tetrahydrofurfuryl, dioxolanyl, oxanyl, and groups of the formula —OM wherein M is phenyl, benzyl, tetrahydrofuryl, dioxolanyl, tetrahydrofurfuryl, oxanyl, or straight or branched alkyl which contains 2 to 6 carbon atoms and a double or triple bond or an ether oxygen and which is optionally substituted with phenyl.

64. A compound according to claim 63 wherein AG is allyloxy, 1-propenyloxy, benzyloxy, oxanyloxy, vinyloxy, phenoxymethoxy, phenoxyethoxy, methoxymethoxy, ethoxymethoxy, tetrahydrofuryloxy, methoxybenzyloxy, dioxolanyl, methoxyethyl, —CH$_2$C≡CH, chlorobenzyloxy, benzyloxyethoxy, —OCH$_2$CH=CHC$_6$H$_5$, or —OCH$_2$CH=CHCH$_3$.

65. A compound according to claim 61 wherein i is 2.

66. A compound according to claim 65 wherein R$^e$ is a chemical bond or alkyl containing 1 to 6 carbon atoms.

67. A compound according to claim 65 wherein AG is divalent alkyl containing 1 to 6 carbon atoms, is optionally interrupted with an ether oxygen, is optionally interrupted by or substituted with phenyl, and optionally contains a double or triple bond.

68. A compound according to claim 67 wherein AG is —OCH$_2$CH≡CHCH$_2$O—, —OCH$_2$C$_6$H$_4$CH$_2$O—, —OCH(C$_6$H$_5$)O—, —OCH$_2$O—, or —OCH$_2$CH=CHCH$_2$O—.

* * * * *